United States Patent
Dellinger et al.

(10) Patent No.: US 10,183,036 B2
(45) Date of Patent: *Jan. 22, 2019

(54) USE OF NICOTINIC ACID RIBOSIDE OR NICOTINAMIDE RIBOSIDE DERIVATIVES, AND REDUCED DERIVATIVES THEREOF, AS NAD+ INCREASING PRECURSORS

(71) Applicant: Chromadex Inc., Irvine, CA (US)

(72) Inventors: Ryan Dellinger, Azusa, CA (US); Troy Rhonemus, Mission Viejo, CA (US); Mark Morris, Irvine, CA (US); Aron Erickson, Longmont, CO (US); Hadi Casser, Northglenn, CO (US); Marie Eugenie Migaud, Armagh (GB)

(73) Assignee: ChromaDex Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/492,952

(22) Filed: Apr. 20, 2017

(65) Prior Publication Data
US 2017/0304338 A1 Oct. 26, 2017

Related U.S. Application Data

(60) Provisional application No. 62/325,264, filed on Apr. 20, 2016.

(51) Int. Cl.
*A01N 43/04* (2006.01)
*A61K 31/70* (2006.01)
*A61K 31/706* (2006.01)

(52) U.S. Cl.
CPC .................................. *A61K 31/706* (2013.01)

(58) Field of Classification Search
None
See application file for complete search history.

(56) References Cited

U.S. PATENT DOCUMENTS

| 7,776,326 | B2 | 8/2010 | Milbrandt et al. |
| 8,383,086 | B2 | 2/2013 | Brenner et al. |
| 2005/0267023 | A1 | 12/2005 | Sinclair et al. |

FOREIGN PATENT DOCUMENTS

| WO | 2015014722 A1 | 2/2015 | |
| WO | WO 2015/186114 A1 * | 12/2015 | ............ C07H 19/048 |
| WO | 2017011788 A1 | 1/2017 | |
| WO | 2017024255 A1 | 2/2017 | |

OTHER PUBLICATIONS

Preiss J et al., Biosynthesis of diphosphopyridine nucleotide. I. Identification of intermediates, J Biol Chem., Aug. 1958, 233(2):488-92.
Schutz G et al., Purification and properties of rat liver tryptophan oxygenase, J Biol Chem., Sep. 10, 1972, 247(17): 5327-32.
Berge SM et al., Pharmaceutical Salts, J Pharm Sci., Jan. 1977, 66(1):1-19.
Ziegler M, New functions of a long-known molecule. Emerging roles of NAD in cellular signaling, Eur J Biochem., Mar. 2000, 267(6):1550-64.
Cohen BH et al., Mitochondrial cytopathy in adults: what we know so far, Cleve Clin J Med., Jul. 2001, 68(7):625-6, 329-42.
Denu JM, Vitamins and aging: pathways to NAD+ synthesis, Cell, May 4, 2007, 129(3):453-4.
Belenky P et al., Nicotinamide Riboside Promotes SIR2 Silencing and Extends Lifespan Via NRK and URH1/PNP1/MEU1 Pathways to NAD+, Cell, May 4, 2007, 129(3):473-84.
EnzyChrom(TM) NAD(+)/NADH Assay Kit (E2ND-100), BioAssay Systems, 2012, 3191 Corporate Place, Hayward, CA94545, USA (Website: www.bioassaysys.com).
Mouchiroud L et al, The NAD(+)/Sirtuin Pathway Modulates Longevity through Activation of Mitochondrial UPR and FOXO Signaling, Cell, Jul. 18, 2013, 154(2):430-41.
Kulikova V et al., Generation, Release, and Uptake of the NAD Precursor Nicotinic Acid Riboside by Human Cells, J Biol Chem, Nov. 6, 2015 (Epub Sep. 18, 2015), 290(45):27124-37.
Substance Record for SID 41017587, PubChem Open Chemistry Database, U.S. National Library of Medicine, National Center for Biotechnology Information, Jun. 12, 2017 Printout.

* cited by examiner

*Primary Examiner* — Patrick T Lewis
(74) *Attorney, Agent, or Firm* — Amin Talati Upadhye LLP; Adam Sussman; George M. Carrera, Jr.

(57) ABSTRACT

Compositions are provided including nicotinic acid riboside ("NAR"), and derivatives thereof including 1-(2',3',5'-triacetyl-beta-D-ribofuranosyl)-nicotinic acid ("NAR triacetate" or "NARTA"); or derivatives of a reduced form of nicotinic acid riboside ("NARH"), including 1-(2',3',5'-triacetyl-beta-D-ribofuranosyl)-1,4-dihydronicotinic acid ("NARH triacetate" or "NARH-TA"); or derivatives of nicotinamide riboside ("NR"), including 1-(2',3',5'-triacetyl-beta-D-ribofuranosyl)-nicotinamide ("NR triacetate" or "NRTA"); derivatives of a reduced form of nicotinamide riboside ("NRH"), including 1-(2',3',5'-triacetyl-beta-D-ribofuranosyl)-1,4-dihydronicotinamide ("NRH triacetate" or "NRH-TA"); or salts or prodrugs thereof, for use in food or beverage applications, pharmaceutical formulations, or as a dietary supplement. Methods of using the compounds above to promote the increase of intracellular levels of nicotinamide adenine dinucleotide ("NAD+") or NADH in cells and tissues for improving cell and tissue survival or overall cell and tissue health are provided.

8 Claims, 10 Drawing Sheets

USE OF NICOTINIC ACID RIBOSIDE OR NICOTINAMIDE RIBOSIDE DERIVATIVES, AND REDUCED DERIVATIVES THEREOF, AS NAD+ INCREASING PRECURSORS

This application claims the benefit of earlier filed U.S. Provisional Application No. 62/325,264, filed on Apr. 20, 2016, which is hereby incorporated by reference herein.

TECHNICAL FIELD

The invention relates to compositions including nicotinic acid riboside ("NAR"), and derivatives thereof including 1-(2',3',5'-triacetyl-beta-D-ribofuranosyl)-nicotinic acid ("NAR triacetate" or "NARTA"); or derivatives of a reduced form of nicotinic acid riboside ("NARH"), including 1-(2',3',5'-triacetyl-beta-D-ribofuranosyl)-1,4-dihydronicotinic acid ("NARH triacetate" or "NARH-TA"); or derivatives of nicotinamide riboside ("NR"), including 1-(2',3',5'-triacetyl-beta-D-ribofuranosyl)-nicotinamide ("NR triacetate" or "NRTA"); derivatives of a reduced form of nicotinamide riboside ("NRH"), including 1-(2',3',5'-triacetyl-beta-D-ribofuranosyl)-1,4-dihydronicotinamide ("NRH triacetate" or "NRH-TA"); or salts or prodrugs thereof, for use in food or beverage applications, pharmaceutical formulations, or as a dietary supplement. The invention further relates to methods of using the compounds above to promote the increase of intracellular levels of nicotinamide adenine dinucleotide ("NAD+") in cells and tissues for improving cell and tissue survival or overall cell and tissue health.

BACKGROUND

Nicotinic acid and nicotinamide, collectively niacins, are the vitamin forms of nicotinamide adenine dinucleotide (NAD+). Eukaryotes can synthesize NAD+de novo via the kynurenine pathway from tryptophan (Krehl, et al. *Science* (1945) 101:489-490; Schutz and Feigelson, *J. Biol. Chem.* (1972) 247:5327-5332) and niacin supplementation prevents the pellagra that can occur in populations with a tryptophan-poor diet. It is well-established that nicotinic acid is phosphoribosylated to nicotinic acid mononucleotide (NaMN), which is then adenylylated to form nicotinic acid adenine dinucleotide (NaAD), which in turn is amidated to form NAD+ (Preiss and Handler, *J. Biol. Chem.* (1958) 233:488-492; Ibid., 493-50).

Nicotinamide Adenine Dinucleotide ("NAD+") is an enzyme co-factor that is essential for the function of several enzymes related to reduction-oxidation reactions and energy metabolism. (Katrina L. Bogan & Charles Brenner, *Nicotinic Acid, Nicotinamide, and Nicotinamide Riboside: A Molecular Evaluation of NAD+ Precursor Vitamins in Human Nutritions*, 28 Annual Review of Nutrition 115 (2008)). NAD+ functions as an electron carrier in cell metabolism of amino acids, fatty acids, and carbohydrates. (Bogan & Brenner 2008). NAD+ serves as an activator and substrate for sirtuins, a family of protein deacetylases that have been implicated in metabolic function and extended lifespan in lower organisms. (Laurent Mouchiroud et al., *The NAD+/Sirtuin Pathway Modulates Longevity through Activation of Mitochondrial UPR and FOXO Signaling*, 154 Cell 430 (2013)). The co-enzymatic activity of NAD+, together with the tight regulation of its biosynthesis and bioavailability, makes it an important metabolic monitoring system that is clearly involved in the aging process.

Once converted intracellularly to $NAD(P)^+$, vitamin B3 is used as a co-substrate in two types of intracellular modifications, which control numerous essential signaling events (adenosine diphosphate ribosylation and deacetylation), and is a cofactor for over 400 reduction-oxidation enzymes, thus controlling metabolism. This is demonstrated by a range of metabolic endpoints including the deacetylation of key regulatory proteins, increased mitochondrial activity, and oxygen consumption. Critically, the NAD(P)(H)-cofactor family can promote mitochondrial dysfunction and cellular impairment if present in sub-optimal intracellular concentrations. Vitamin B3 deficiency yields to evidenced compromised cellular activity through $NAD^+$ depletion, and the beneficial effect of additional $NAD^+$ bioavailability through nicotinic acid ("NA"), nicotinamide ("Nam"), and nicotinamide riboside ("NR") supplementation is primarily observed in cells and tissues where metabolism and mitochondrial function had been compromised.

Interestingly, supplementation with nicotinic acid ("NA") and nicotinamide ("Nam"), while critical in acute vitamin B3 deficiency, does not demonstrate the same physiological outcomes compared with that of nicotinamide riboside ("NR") supplementation, even though at the cellular level, all three metabolites are responsible for $NAD^+$ biosynthesis. This emphasizes the complexity of the pharmacokinetics and bio-distribution of B3-vitamin components.

The bulk of intracellular $NAD^+$ is believed to be regenerated via the effective salvage of nicotinamide ("Nam") while de novo $NAD^+$ is obtained from tryptophan. (Anthony Rongvaux et al., *Reconstructing eukaryotic NAD metabolism*, 25 BioEssays 683 (2003)). Crucially, these salvage and de novo pathways apparently depend on the functional forms of vitamins B1, B2, and B6 to generate $NAD^+$ via a phosphoriboside pyrophosphate intermediate. Nicotinamide riboside ("NR") is the only form of vitamin B3 from which $NAD^+$ can be generated in a manner independent of vitamins B1, B2, and B6, and the salvage pathway using nicotinamide riboside ("NR") for the production of $NAD^+$ is expressed in most eukaryotes.

The main $NAD^+$ precursors that feed the salvage pathways are nicotinamide ("Nam") and nicotinamide riboside ("NR"). (Bogan & Brenner 2008). Studies have shown that nicotinamide riboside ("NR") is used in a conserved salvage pathway that leads to $NAD^+$ synthesis through the formation of nicotinamide mononucleotide ("NMN"). Upon entry into the cell, nicotinamide riboside ("NR") is phosphorylated by the NR kinases ("NRKs"), generating NMN, which is then coverted to $NAD^+$ by nicotinamide mononucleotide adenylyltransferase ("NMNAT"). (Bogan & Brenner 2008). Because NMN is the only metabolite that can be converted to $NAD^+$ in mitochondria, nicotinamide ("Nam") and nicotinamide riboside ("NR") are the two candidate $NAD^+$ precursors that can replenish $NAD^+$ and thus improve mitochondrial fuel oxidation. A key difference is that nicotinamide riboside ("NR") has a direct two-step pathway to $NAD^+$ synthesis that bypasses the rate-limiting step of the salvage pathway, nicotinamide phosphoribosyltransferase ("NAMPT"). Nicotinamide ("Nam") requires NAMPT activity to produce $NAD^+$. This reinforces the fact that nicotinamide riboside ("NR") is a very effective $NAD^+$ precursor. Conversely, deficiency in dietary $NAD^+$ precursors and/or tryptophan causes pellagra, a disease characterized by dermatitis, diarrhea, and dementia. (Bogan & Brenner 2008). In summary, $NAD^+$ is required for normal mitochondrial function, and because mitochondria are the powerhouses of the cell, $NAD^+$ is required for energy production within cells.

NAD+ was initially characterized as a co-enzyme for oxidoreductases. Though conversions between NAD+, NADH, NADP and NADPH would not be accompanied by a loss of total co-enzyme, it was discovered that NAD+ is also turned over in cells for unknown purposes (Maayan, *Nature* (1964) 204:1169-1170). Sirtuin enzymes such as Sir2 of *S. cerevisiae* and its homologs deacetylate lysine residues with consumption of an equivalent of NAD+ and this activity is required for Sir2 function as a transcriptional silencer (Imai, et al., *Cold Spring Harb. Symp. Quant. Biol.* (2000) 65:297-302). NAD+-dependent deacetylation reactions are required not only for alterations in gene expression but also for repression of ribosomal DNA recombination and extension of lifespan in response to calorie restriction (Lin, et al., *Science* (2000) 289:2126-2128; Lin, et al., *Nature* (2002) 418:344-348). NAD+ is consumed by Sir2 to produce a mixture of 2'- and 3' 0-acetylated ADP-ribose plus nicotinamide and the deacetylated polypeptide (Sauve, et al., *Biochemistry* (2001) 40:15456-15463). Additional enzymes, including poly(ADPribose) polymerases and cADPribose synthases are also NAD+-dependent and produce nicotinamide and ADPribosyl products (Ziegler, *Eur. J. Biochem.* (2000) 267:1550-1564; Burkle, *Bioessays* (2001) 23:795-806).

The non-coenzymatic properties of NAD+ has renewed interest in NAD+ biosynthesis. FIG. 1 describes how NAR, NR and other metabolic intermediates are transformed to NAD+. In short, the biosynthetic pathway for NAR proceeds directly to NaMN, then NaAD, and ultimately to form NAD+.

Recently NAR was shown to be an NAD+ precursor (V. Kulikova, et al., *J. Biol. Chem., Papers in Press*, publ. on Sep. 18, 2015). Kulikova, et al. demonstrated that NAR supports cell survival at low micromolar concentrations (about 1 micromolar), whereas 10 times more NR was required to maintain viability. Kulikova, et al. also demonstrated that NAR can produce NAD+ independently of NAPRT (as NR can produce NAD+ independently of NAMPRT a.k.a. Nampt, albeit at higher concentrations).

If NAR, or its derivatives, salts, or prodrugs thereof, as described herein, could be used in pharmacueticals, food or beverages, or dietary supplements to enhance NAD+ levels in cells, this would represent a useful contribution to the art.

SUMMARY

In an embodiment, the present disclosure provides a pharmaceutical composition containing NAR in combination with a carrier, which increases NAD+ levels upon administration.

In another embodiment, a method is provided for increasing intracellular NAD+ in a subject mammal, comprising the steps of delivering to the individual in need of such treatment an effective amount of at least one compound of formula (Ia) or a salt, solvate, or prodrug thereof:

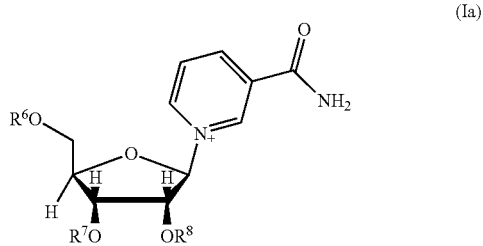

(Ia)

or, a compound of formula (IIa), or a salt, solvate, or prodrug thereof:

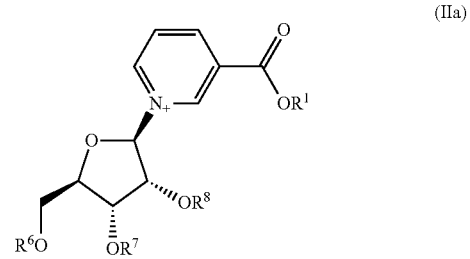

(IIa)

wherein $R^1$, $R^6$, $R^7$, and $R^8$ are as described hereinbelow; and wherein NAD+ biosynthesis is increased.

BRIEF DESCRIPTIONS OF THE DRAWINGS

DETAILED DESCRIPTION

Figure 1:
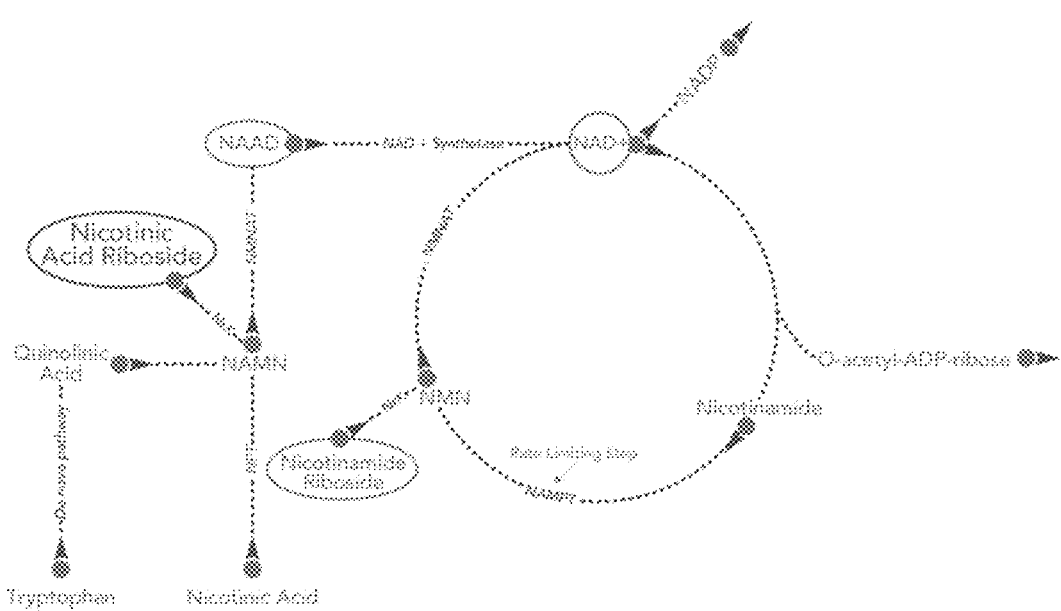
FIG. 1 depicts the $NAD^+$ biosynthetic pathway. Nicotinic acid riboside (NAR) and nicotinamide riboside (NR) are shown.
Figure 2:
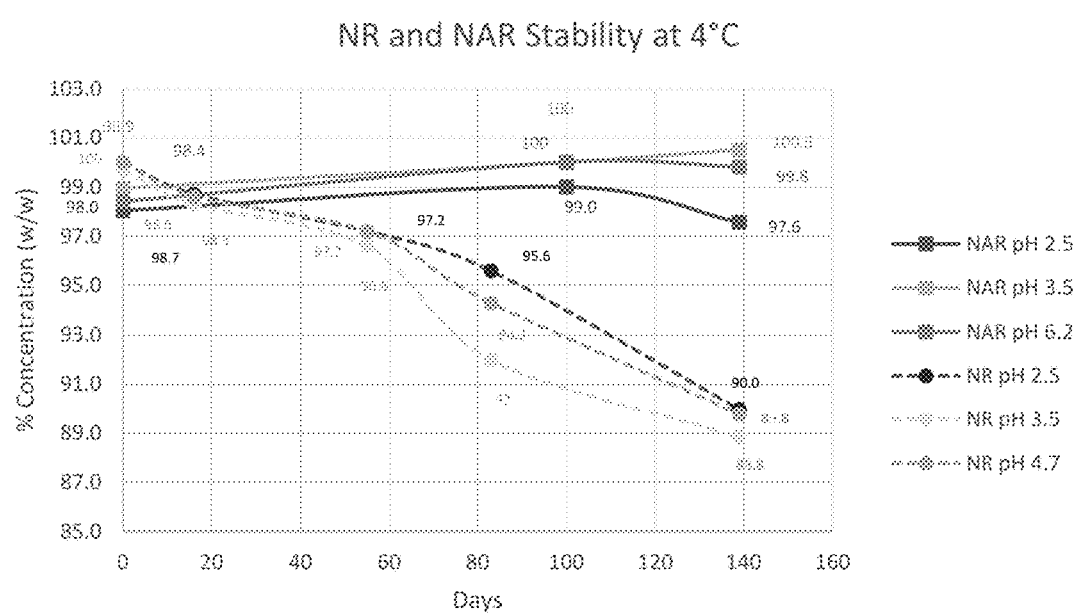
FIG. 2 depicts in one embodiment concentration (% wt/wt) over time in days of NAR and NR showing temperature stability in aqueous solution at 4° C., where pH is varied at 2.5, 3.5 and 6.2 for NAR, and pH is varied at 2.5, 3.5 and 4.7 for NR.
Figure 3:
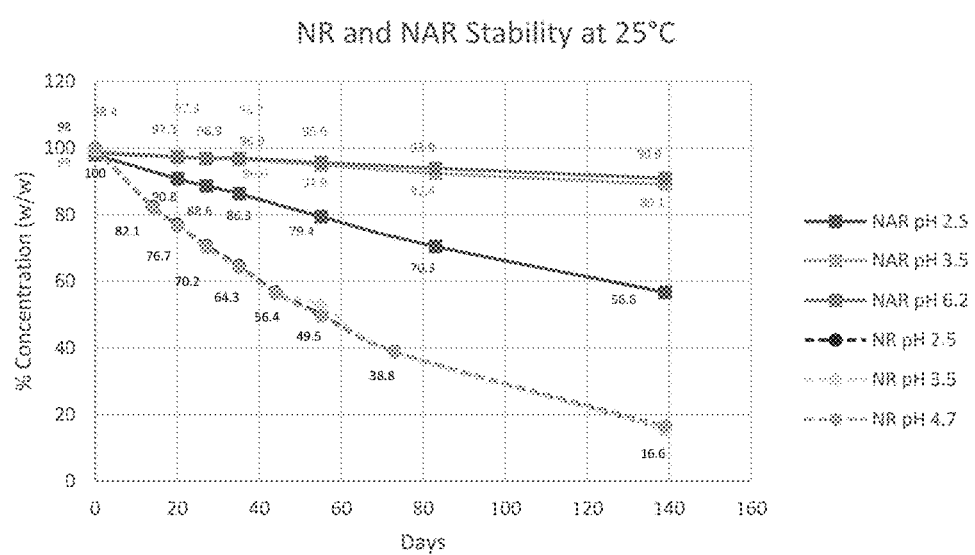
FIG. 3 depicts in another embodiment concentration (% wt/wt) over time in days of NAR and NR showing temperature stability in aqueous solution at 25° C., where pH is varied at 2.5, 3.5 and 6.2 for NAR, and pH is varied at 2.5, 3.5 and 4.7 for NR.
Figure 4:
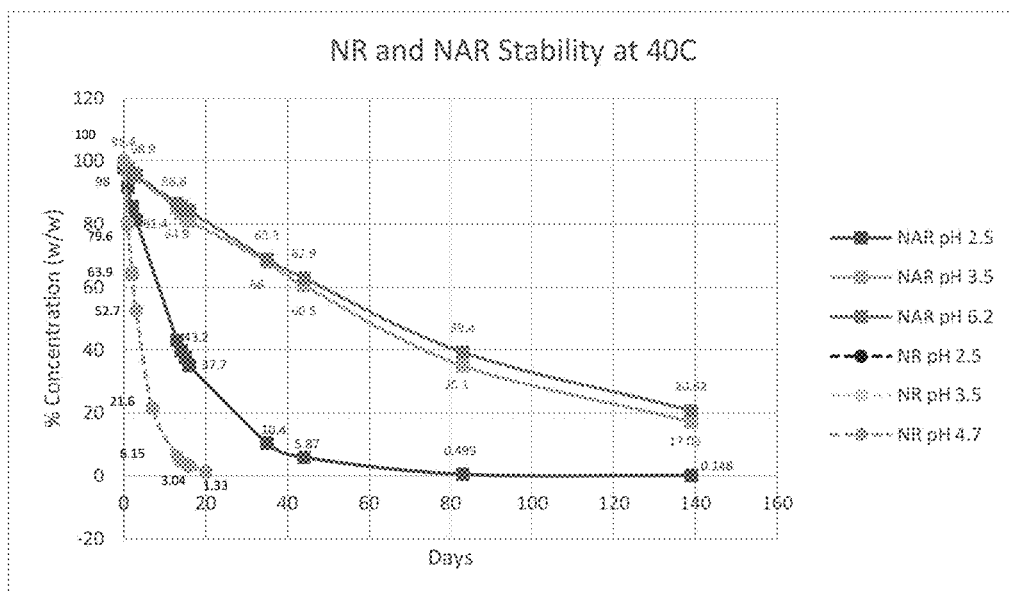
FIG. 4 depicts in another embodiment concentration (% wt/wt) over time in days of NAR and NR showing temperature stability in aqueous solution at 40° C., where pH is varied at 2.5, 3.5 and 6.2 for NAR, and pH is varied at 2.5, 3.5 and 4.7 for NR.
Figure 5:
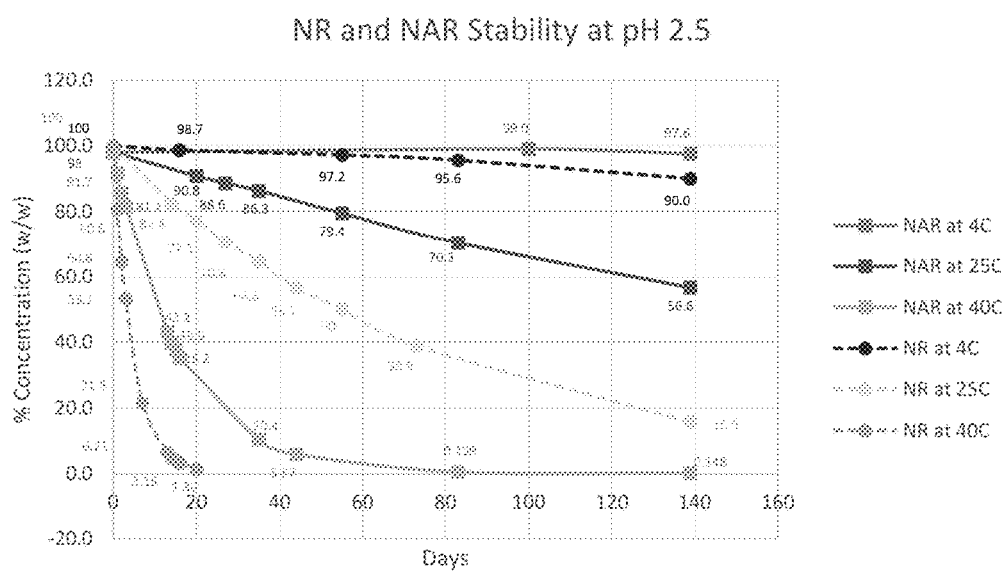
FIG. 5 depicts in another embodiment concentration (% wt/wt) over time in days of NAR and NR showing pH stability in aqueous solution at pH 2.5, where temperature is varied at 4° C., 25° C. and 40° C.
Figure 6:
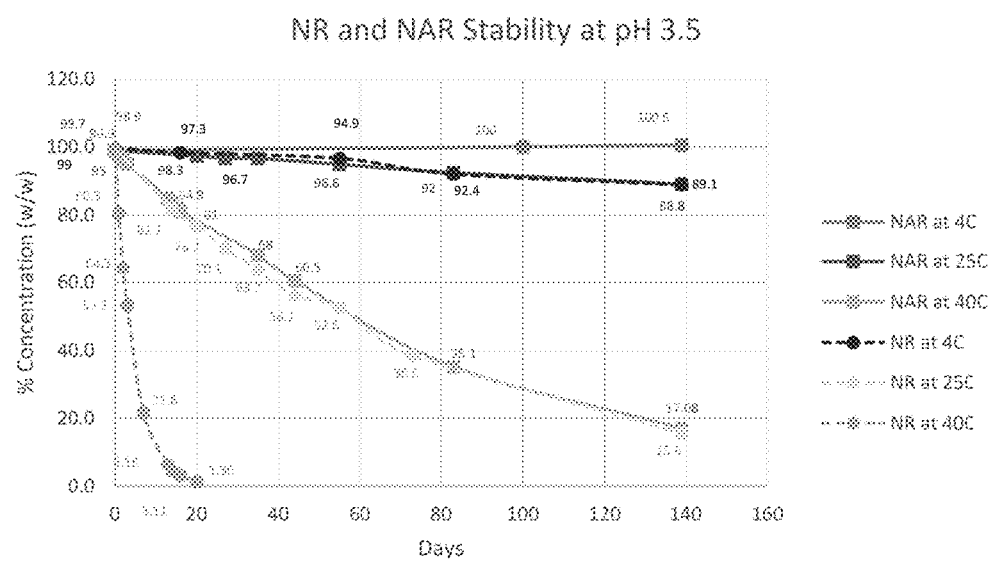
FIG. 6 depicts in another embodiment concentration (% wt/wt) over time in days of NAR and NR showing pH stability in aqueous solution at pH 3.5, where temperature is varied at 4° C., 25° C. and 40° C.
Figure 7:
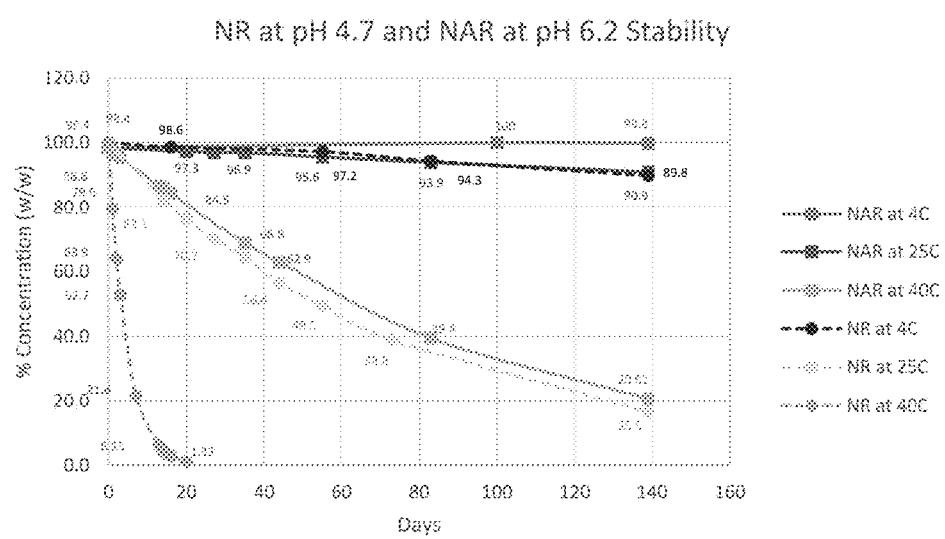
FIG. 7 depicts in another embodiment concentration (% wt/wt) over time in days of NAR and NR showing pH stability in aqueous solution at pH 4.7 (NR) and pH 6.2 (NAR), where temperature is varied at 4° C., 25° C. and 40° C.

In one aspect, compositions are provided including nicotinic acid riboside ("NAR"), and derivatives thereof including 1-(2',3',5'-triacetyl-beta-D-ribofuranosyl)-nicotinic acid ("NAR triacetate" or "NARTA"); or derivatives of a reduced form of nicotinic acid riboside ("NARH"), including 1-(2', 3',5'-triacetyl-beta-D-ribofuranosyl)-1,4-dihydronicotinic acid ("NARH triacetate" or "NARH-TA"); or derivatives of nicotinamide riboside ("NR"), including 1-(2',3',5'-triacetyl-beta-D-ribofuranosyl)-nicotinamide ("NR triacetate" or "NRTA"); derivatives of a reduced form of nicotinamide riboside ("NRH"), including 1-(2',3',5'-triacetyl-beta-D-ribofuranosyl)-1,4-dihydronicotinamide ("NRH triacetate" or "NRH-TA"); or salts or prodrugs thereof, for use in food or beverage applications, pharmaceutical formulations, or as a dietary supplement. Nicotinamide riboside used as a single active ingredient is hereby excluded.

Methods of using the compounds above are herein provided to promote the increase of intracellular levels of nicotinamide adenine dinucleotide ("NAD+") in cells and tissues for improving cell and tissue survival and overall cell and tissue health.

In further embodiments, there are provided pharmaceutical compositions containing NAR, NRH, and/or NARH derivatives, NR derivatives, prodrugs, solvates, or salts thereof. In further embodiments, the invention relates to methods of using NAR, NRH, and/or NARH derivatives, NR derivatives, prodrugs, or salts thereof to promote the increase of intracellular levels of nicotinamide adenine dinucleotide (NAD+) in cells and tissues for improving cell and tissue survival and overall cell and tissue health. In further embodiments, the invention relates to derivatives of other established NAD+ precursor molecules ("NMN," "NaMN," and their reduced forms) that would increase or enhance intracellular levels of NAD+.

Cells that may be treated to extend their lifespans or protect against apoptosis include normal, healthy mammalian (or human) cells, or genetically modified cells or organisms such as single cell bacteria or yeasts, for example. Other cells that may be treated to extend their lifespans or protect against apoptosis include cells for production, consumption, or food, e.g., cells from non-human mammals (such as meat), or plant cells (such as vegetables). Treatment of cell based tissues or organ systems is contemplated. Treatment of diseased, growth arrested, or immunocompromised cells is contemplated.

In another embodiment, the compounds described herein may be used in cell culture to upregulate NAD+.

In a further embodiment, the compounds described herein may be used for "in vitro fertilization" (IVF) procedures, e.g., ex vivo cell culture.

Nicotinamide riboside ("NR") is a pyridinium compound having the formula (I):

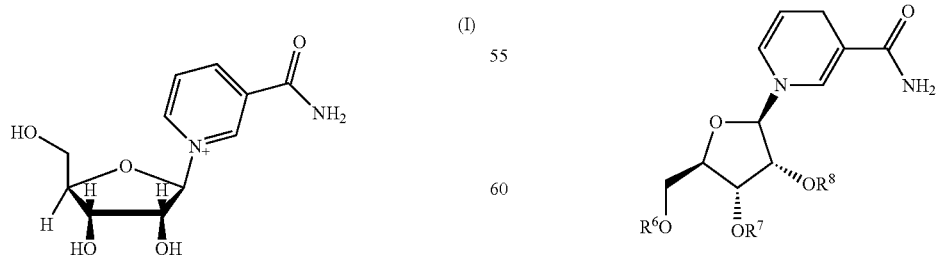

Nicotinamide riboside ("NR") is available in a reduced form ("NRH") as a 1,4-dihydropyridine compound having the formula (I-H):

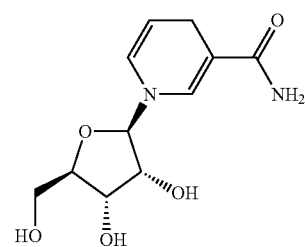

In a particular aspect, the compound (I) can be further derivatized to NR derivatives, prodrugs, or salts thereof, having the formula (Ia):

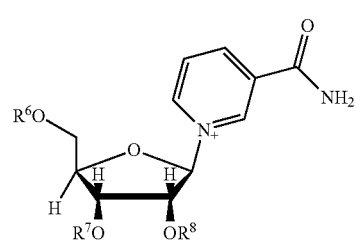

wherein $R^6$ is selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, and substituted or unsubstituted heterocycle;

R' is selected from the group consisting of hydrogen, —$(C_1-C_8)$alkyl, —$(C_1-C_8)$cycloalkyl, aryl, heteroaryl, heterocycle, aryl$(C_1-C_4)$alkyl, and heterocycle$(C_1-C_4)$alkyl; and $R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_1-C_8)$cycloalkyl, substituted or unsubstituted aryl, substituted or unsubstituted heteroaryl, substituted or unsubstituted heterocycle, substituted or unsubstituted aryl$(C_1-C_4)$alkyl, and substituted or unsubstituted heterocycle$(C_1-C_4)$alkyl.

In a particular aspect, the compound (I-H) can be further derivatized to NRH derivatives, prodrugs, or salts thereof having the formula (I-Ha):

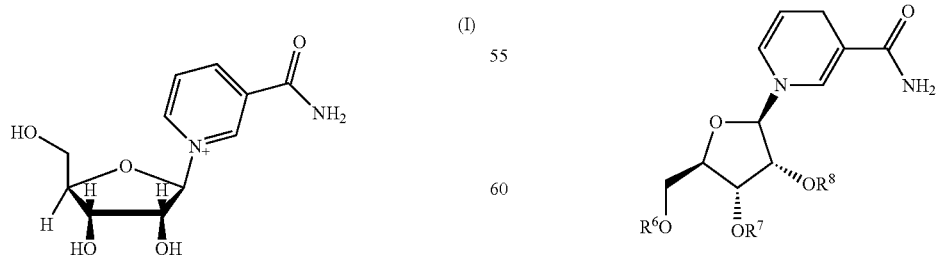

wherein $R^6$, R', $R^7$, and $R^8$ are as defined above for the compounds having the formulas (Ia).

In one preferred embodiment, the free hydrogens of hydroxyl groups on the ribose moiety can be substituted with acetyl groups ($CH_3$—C(=O)—) in a nicotinamide riboside compound having formula (I) to form compounds having formula (Ia), specifically 2',3',5'-tri acetyl-nicotinamide riboside ("NR triacetate" or "NRTA"), having the formula (1). Alternative names include: 1-(2',3',5'-triacetyl-beta-D-ribofuranosyl)-nicotinamide, or 1-(3-carboxamido-pyridin-1-yl)-beta-D-riboside-2',3',5'-triacetate ("NR triacetate" or "NRTA," 1) all having the formula (1):

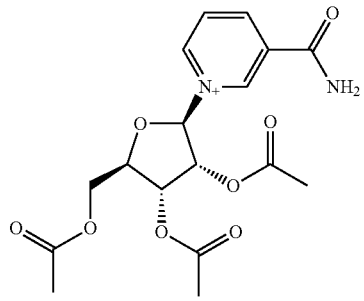

(1)

In another preferred embodiment, the free hydrogens of hydroxyl groups on the ribose moiety can be substituted with acetyl groups ($CH_3$—C(=O)—) in a 1,4-dihydronicotinamide compound having formula (I-H) to form compounds having formula (I-Ha), specifically 2',3',5'-triacetyl-1,4-dihydronicotinamide riboside ("NRH triacetate" or "NRH-TA"), having the formula (2). Alternative names include: 1-(2',3',5'-triacetyl-beta-D-ribofuranosyl)-1,4-dihydronicotinamide, or 1-(3-carboxamido-1,4-dihydropyridin-1-yl)-beta-D-riboside-2',3',5'-triacetate ("NRH triacetate" or "NRH-TA," 2) all having the formula (2):

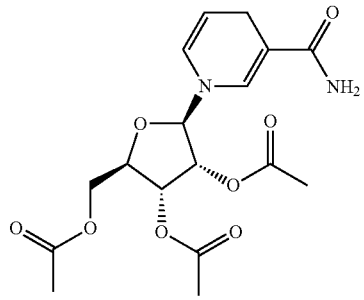

(2)

The compound of formula (2) was prepared in accordance with WO 2015/014722, which is hereby incorporated by reference herein.

Nicotinic acid riboside ("NaR," or "NAR") is a pyridinium compound having the formula (II):

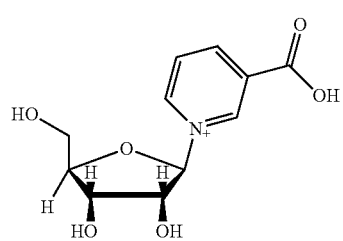

(II)

Nicotinic acid riboside ("NAR") is available in a reduced form ("NARH") as a 1,4-dihydropyridine compound having the formula (II-H):

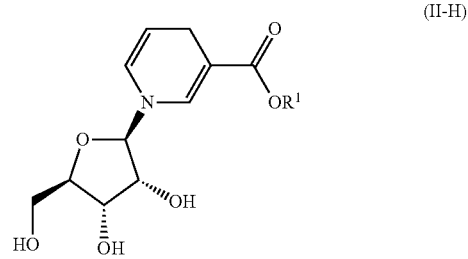

(II-H)

wherein $R^1$ is selected from hydrogen (II-Ha) and ($C_1$-$C_4$)alkyl (II-Hb), and prodrugs or salts thereof.

Compounds having the formula (II-H) may be prepared in accordance with WO 2015/014722, which is incorporated by reference. Depending on the selection of $R^1$, compounds having the formula (II-H): include alkyl 1-(beta-D-ribofuranosyl)-1,4-dihydronicotinates or alternatively alkyl 1,4-dihydronicotinate riboside ("alkyl NARH") where $R^1$ is selected from ($C_1$-$C_4$)alkyl (II-Hb); and include 1-(beta-D-ribofuranosyl)-1,4-dihydronicotinic acid where $R^1$ is selected from hydrogen (II-Ha).

In a particular aspect, a compound having the formula (II) can be further derivatized to NAR derivatives, prodrugs, solvates, or salts thereof having the formula (IIa):

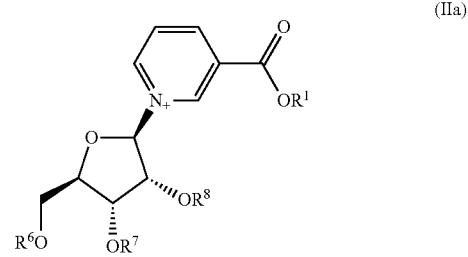

(IIa)

wherein $R^1$, $R^6$, $R'$, $R^7$, and $R^8$ are as defined above for compounds having the formulas (Ia), (I-Ha), and (II-H).

In a preferred embodiment, the free hydrogens of hydroxyl groups on the ribose moiety of a compound having formula (II) can be substituted with acetyl groups ($CH_3$—C(=O)—) in a nicotinic acid riboside compound to form an NAR derivative, prodrug, or salt thereof, having the formula (IIa), specifically 1-(2',3',5'-triacetyl-beta-D-ribofuranosyl)-nicotinic acid ("NAR triacetate" or "NARTA") where $R^1$ is hydrogen, having the formula (3). Alternative names include: 1-(2',3',5')-triacetyl-beta-D-ribofuranosyl)-nicotinic acid, or 1-(3-carboxyl-pyridin-1-yl)-beta-D-riboside-2',3',5'-triacetate ("NAR triacetate" or "NARTA," 3) all having the formula (3):

(3)

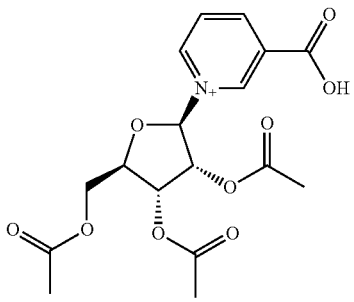

In a particular aspect, a compound having the formula (II-H) can be further derivatized to NARH derivatives, prodrugs, solvates, or salts thereof having the formula (II-Hc):

(II-Hc)

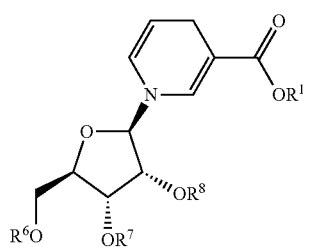

wherein $R^1$, $R^6$, $R'$, $R^7$, and $R^8$ are as defined above for the compounds having the formulas (Ia), (I-Ha), (II-H), and/or (IIa).

In one preferred embodiment, the free hydrogens of hydroxyl groups on the ribose moiety of a compound having formula (II-H) can be substituted with acetyl groups ($CH_3$—C(=O)—) in a 1,4-dihydropyridine compound to form an NARH derivative, prodrug, solvate, or salt thereof, having the formula (II-Hc), specifically a compound having formula (4), which, depending on the selection of $R^1$: include alkyl 2%3%5'-triacetyl-1,4-dihydronicotinate riboside ("alkyl NARH triacetate"), alternatively called alkyl 1-(2',3',5'-triacetyl-beta-D-ribofuranosyl)-1,4-dihydronicotinate ("alkyl NARH triacetate"), where $R^1$ is selected from ($C_1$-$C_4$)alkyl; and include 2',3',5'-triacetyl-1,4-dihydronicotinic acid riboside ("NARH triacetate" or "NARH-TA"), alternatively called 1-(2',3',5'-triacetyl-beta-D-ribofuranosyl)-1,4-dihydronicotinic acid ("NARH triacetate" or "NARH-TA"), where $R^1$ is selected from hydrogen (4)

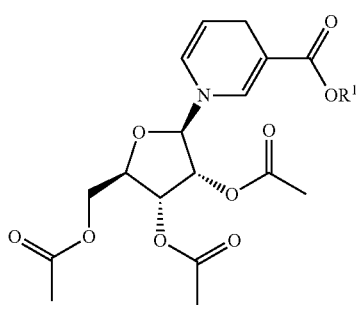

wherein $R^1$ is selected from hydrogen and ($C_1$-$C_4$)alkyl, and salts, solvates, or prodrugs thereof.

In a particularly preferred embodiment, $R^1$ is hydrogen (compound 4a), also known as 2',3',5'-triacetyl-1,4-dihydronicotinic acid riboside ("NARH triacetate" or "NARH-TA," 4a), or 1-(2',3',5'-triacetyl-beta-D-ribofuranosyl)-1,4-dihydronicotinic acid, or alternatively 1-(3-carboxy-1,4-dihydropyridin-1-yl)-beta-D-riboside-2',3',5'-triacetate ("NARH triacetate" or "NARH-TA," 4a). The compound of formula (4a) was prepared in accordance with WO 2015/014722, which is hereby incorporated by reference herein.

The compounds having formula (4) where $R^1$ is hydrogen ("NARH triacetate," "NARH-TA," 4a) may also exist as a conjugate base salt wherein hydrogen is replaced with a salt counterion such as, but not limited to, sodium, potassium, lithium, magnesium, and the like. Reference is made to: the latest edition of REMINGTON'S PHARMACEUTICAL SCIENCES (Mack Publishing Co., Easton, Pa.); S. Berge et al., *Pharmaceutical Salts*, 66 J. PHARM. SCI. 1 (1977) (and references cited therein); and L. D. Bighley, et al., *Salt Forms of Drugs and Absorption*, in ENCYCLOPEDIA PHARM. TECH. VOL. 13 453 (J. Swarbrick ed., Marcel Dekker, Inc. 1996) (and references cited therein); all incorporated by reference herein.

In an embodiment, compounds having formulas selected from (Ia), (I-Ha), (IIa), (II-H), (II-Ha), (II-Hb), and (II-Hc) possess certain properties believed to enhance biosynthesis of NAD+ in vivo or in vitro. For example, these compounds have increased lipophilicity in their reduced forms.

In another aspect, the compounds having formulas selected from (Ia), (I-Ha), (IIa), (II-II), (II-Ha), (II-Hb), and (II-Hc) are useful as NAD+ precursors for providing certain health benefits. Since NAD+ levels decrease with age or aging processes, it is expected that supplementation with one of more of the compounds will help maintain healthy NAD+ levels in a subject.

Without being bound by theory, it is believed that, as can be seen in the $NAD^+$ biosynthetic pathway depicted in FIG. 1, nicotinamide riboside ("NR," I) converts to nicotinamine mononucleotide ("NMN," III) via phosphorylation by NR kinases ("NRKs"). Nicotinamide mononucleotide ("NMN," III) is then converted to $NAD^+$ by nicotinamide mononucleotide adenylyltransferase ("NMNAT"). Nicotinamide mononucleotide ("NMN," III) is the only metabolite that can be converted to $NAD^+$ in mitochondria, thus nicotinamide and nicotinamide riboside ("NR," I) are the two candidate $NAD^+$ precursors that can replenish $NAD^+$ and improve mitochondrial fuel oxidation. However, nicotinamide riboside ("NR," I) has a direct two step pathway to $NAD^+$ synthesis that bypasses the rate-limiting step of the salvage pathway, conversion of nicotinamide to nicotinamide mononucleotide ("NMN," III) via activity of nicotinamide phosphoribosyltransferase ("NAMPT"). Kulikova, et al. (in press, 2015) also demonstrated that NAR can produce NAD+ independently of NAPRT (as NR can produce NAD+ independently of NAMPRT a.k.a. Nampt, albeit at higher concentrations). FIG. 1 further describes how NAR, NR and other metabolic intermediates are transformed to NAD+. In short, the biosynthetic pathway for NAR proceeds directly to NaMN, then NaAD, and ultimately to form NAD+.

In an alternative embodiment, and without being bound by theory, the use of reduced (1,4-dihydro) forms of NR or NAR such as NRH and NARH, or the like, including other reduced nicotinyl ribosides may be mediated by an alternative biosynthetic pathway to produce NAD+, or in a bypass mechanism, NADH directly. It has been shown that reduced nicotinyl ribosides are poor substrates for NRK1 and 2 (unpublished data). A non-NRK mediated pathway has been proposed to NADH which may bypass known NAD-producing routes via a reduced form of NMN (i.e. "NMNH"). For example, NRH could enter the cell using a nucleoside transporter, then be a substrate for a non-NRK nucleoside kinase to convert to NMNH. In the same manner, NARH could be converted to NAMNH. In an extension of this hypothesis, NMNH would be converted directed to NADH, thus bypassing NAD metabolism. Finally, increased NADH production can ultimately raise NAD+ levels using this alternate mechanism.

One way of delivering NAD+ precursors is as a food or beverage, or a dietary supplement. NAR is a useful NAD+ precursor for such uses. Several formulation studies were done in order to test for stability of NAR in aqueous solution at various temperature and pH conditions in comparison to NR, as follows.

Example 1

Nicotinamide riboside (NR) was prepared in 1000 ppm aqueous solution (w/v) at 2.5, 3.5 and 4.7 pH levels. Nicotinic acid riboside (NAR) was prepared n 1000 ppm aqueous solution (w/v) at 2.5, 3.5 and 6.2 pH levels. The six sample solutions were aliquoted into various small sealed vials to be used as individual sample pull points for analysis. The sample solution aliquots were maintained at 4° C., 25° C. and 40° C. for the duration of the study as indicated in FIGS. 2-7. The concentrations of NR and NAR, respectively, were monitored throughout the study as indicated in FIGS. 2-7.

Results

NAR exhibited much greater stability at low temperature (4° C.) and ambient temperature (25° C.) at all measured pH levels in comparison to NR. At 4° C. NAR assay was greater than 95% after 140 days. Generally at higher temperature and lower pH, the stability of NAR was markedly decreased over time in weeks; however, NAR stability consistently exceed NR stability when compared under the same testing parameters.

In a further embodiment, compositions containing NAR, or derivatives thereof, may be stabilized by the addition of certain excipients or additives. Useful additives may include, but are not limited to, whey protein, casein, and the like.

In certain embodiments, for one or more nicotinyl compounds (I derivative, II, and/or III) or derivatives, prodrugs or salts thereof, binding of whey and/or casein protein can also be used to stabilize the one or more compounds in any liquid formulation. The addition of these proteins in particular (either alone or in combination with other proteins) in order to stabilize nicotinyl compounds (I derivative, II, and/or III) or derivatives, prodrugs or salts thereof, in liquid constitutes another embodiment of a method of delivery of the present invention. Useful formulations may include dietary supplements, beverages, energy drinks, and the like.

In one aspect, the present invention surprisingly demonstrates novel methods for delivering NAD+-precursors to a subject mammal in need thereof. In a particular embodiment, methods for delivering at least one compound selected from nicotinamide riboside ("NR"), nicotinic acid riboside ("NAR"), and nicotinamide mononucleotide ("NMN"), or derivatives thereof, or reduced pyridine derivatives thereof, or salts, solvates, or prodrugs thereof, to a subject in need of said compound or compounds are described. In another embodiment, the invention relates to methods for delivering at least one compound selected from NR, NAR, and NMN, or derivatives thereof, or reduced pyridine derivatives thereof, or salts, solvates, or prodrugs thereof, in combination with at least one of thiamine (vitamin B1), riboflavin (vitamin B2), niacin (vitamin B3), and pyridoxine (vitamin B6) to a subject in need of said compound or compounds. In yet another embodiment, the invention relates to methods for treating and/or preventing symptoms, diseases, disorders, or conditions associated with, or having etiologies involving, vitamin B3-deficiency and/or that would benefit from increased mitochondrial activity.

Without being bound by theory, in another embodiment, it is believed that administering or delivering at least one compound selected from nicotinamide riboside derivatives ("NR (I) derivatives"), nicotinic acid riboside ("NAR," II), and nicotinamide mononucleotide ("NMN," III), or derivatives thereof (including "reduced" 1,4-dihydropyridyl), or salts thereof, or alternatively with compounds having formulas selected from (Ia), (I-Ha), (IIa), (II-H), (II-Ha), (II-Hb), and (II-Hc), would treat and/or prevent symptoms, diseases, disorders, or conditions associated with, or having etiologies involving, vitamin B3 deficiency and/or that would benefit from increased mitochondrial activity. As used in the present specification, the term "derivative" can include a prodrug, or a reduced derivative as described above.

Vitamin B3, which is also known as nicotinic acid, or niacin, is a pyridine compound having the formula (IV):

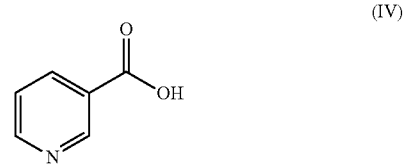

(IV)

Without being bound by theory, it is believed that, as can be seen in the NAD+ biosynthetic pathway depicted in FIG. 1, vitamin B3 ("nicotinic acid," or "niacin," IV) is converted via several intermediates to NAD+. Niacin is also known to include an admixture with nicotinamide ("Nam"). For the purposes of this disclosure, it may be appreciated by one of skill in the art that Vitamin B3 can also include or consist of nicotinamide (Nam) or nicotinamide riboside (NR, I). These variant terms may be used synonymously or interchangeably where required to describe effective compositions or mixtures for use in the embodiments of the invention.

Vitamin B1, which is also known as thiamine, is a compound having the formula (V):

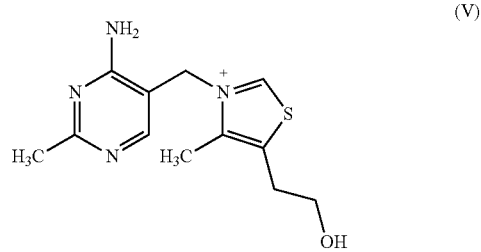

(V)

Vitamin B2, which is also known as riboflavin, is a compound having the formula (VI):

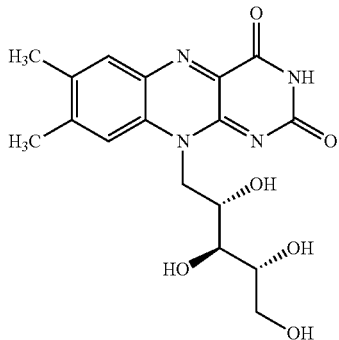

(VI)

Vitamin B6, which is also known as pyridoxine in the form most commonly given as a supplement, is a compound having the formula (VII):

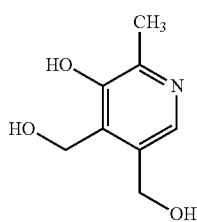

(VII)

Without being bound by theory, in yet another embodiment, it is believed that food or beverage products containing at least one compound selected from nicotinamide riboside derivatives ("NR (I) derivatives"), nicotinic acid riboside ("NAR," II), and nicotinamide mononucleotide ("NMN," III), or salts thereof, used in combination with each other, or alternatively with compounds having formulas selected from (Ia), (I-Ha), (IIa), (II-H), (II-Ha), (II-Hb), and (II-Hc), or alternatively with one or more vitamins selected from vitamin B1 ("thiamine," V), vitamin B2 ("riboflavin," VI), vitamin B3 ("nicotinic acid" or "niacin," IV), and vitamin B6 ("pyridoxine" in supplement form, VII) would effectively provide higher levels of $NAD^+$ to a subject in need thereof than when provided separately, in a synergistic manner.

It is expected that delivering at least one compound selected from nicotinamide riboside derivatives ("NR (I) derivatives"), nicotinic acid riboside ("NAR," II), and nicotinamide mononucleotide ("NMN," III), or salts thereof, or alternatively with compounds having formulas selected from (Ia), (I-Ha), (IIa), (II-H), (II-Ha), (II-Hb), and (II-Hc), optionally in combination with one or more vitamins selected from vitamin B1 ("thiamine," V), vitamin B2 ("riboflavin," VI), vitamin B3 ("nicotinic acid" or "niacin," IV), and vitamin B6 ("pyridoxine" in supplement form, VII) would effectively provide higher levels of $NAD^+$ to a subject in need thereof than when provided separately, and higher levels of $NAD^+$ than either a nicotinyl compound (I derivative, II, and/or III), or derivatives thereof (including "reduced" derivatives), or salts or prodrugs thereof, or a vitamin (IV, V, VI, and/or VII) alone.

Definitions

As used in the specification and the appended claims, the singular forms of "a," "an," and "the" include plural referents unless the context clearly dictates otherwise.

As used herein, the term "nicotinyl" and "nicotinoyl" are interchangeable. One useful example is 3-nicotinoyl, or 3-nicotinyl, in which a carbonyl group (C=O) can serve as a linker at the 3-position of pyridine. Further, the term "nicotinyl riboside" can encompass nicotinamide riboside or nicotinic acid riboside, for example.

As used herein, the terms "nutraceutically acceptable carrier" and "pharmaceutically acceptable carrier" mean any carrier, diluent, or excipient that is compatible with the other ingredients of the formulation and not deleterious to the user. Useful excipients include microcrystalline cellulose, magnesium stearate, calcium stearate, any acceptable sugar (e.g., mannitol, xylitol), and for cosmetic use, an oil-base is preferred.

As used herein, the term "alkyl," by itself or as part of another substituent, means, unless otherwise stated, a straight, branched, or cyclic chain hydrocarbon (cycloalkyl) having the number of carbon atoms designated (i.e., $C_1$-$C_6$ means one to six carbons). Examples include methyl, ethyl, propyl, isopropyl, butyl, isobutyl, tert-butyl, pentyl, neopentyl, hexyl, cyclohexyl, and cyclopropyl. Most preferred are ($C_1$-$C_3$)alkyl, particularly ethyl, ethyl, and isopropyl.

As used herein, the term "alkenyl," by itself or as part of another substituent, means, unless otherwise stated, a stable mono-unsaturated or di-unsaturated straight chain, the unsaturation meaning a carbon-carbon double bond (—CH=CH—), branched chain or cyclic hydrocarbon group having the stated number of carbon atoms. Examples include vinyl, propenyl (allyl), crotyl, isopentenyl, butadienyl, 1,3-pentadienyl, 1,4-pentadienyl, cyclopentenyl, cyclopentadienyl, and the higher homologs and isomers. Functional groups representing an alkene are exemplified by —CH=CH—$CH_2$— and $CH_2$=CH—$CH_2$—.

As used herein, the terms "substituted alkyl" or "substituted alkenyl" mean "alkyl" or "alkenyl," respectively, as defined above, substituted by one, two, or three substituents. The substituents may, for example, be selected from the group consisting of halogen, —OH, —$NH_2$, —$N(CH_3)_2$, —$CO_2H$, —$CO_2(C_1$-$C_4)$alkyl, methoxy, ethoxy, trifluoromethyl, —C(=O)$NH_2$, —$SO_2NH_2$, —C(=NH)$NH_2$, —C≡N, and —$NO_2$, preferably selected from halogen and —OH. Examples of substituted alkyls include, but are not limited to, 2,2-difluoromethyl, 2-carboxycyclopentyl, and 3-chloropropyl.

As used herein, the term "alkynyl," by itself or as part of another substituent, means, unless otherwise stated, a stable carbon-carbon triple bond-containing radical (—C≡C—), branched chain or cyclic hydrocarbon group having the stated number of carbon atoms. Examples include ethynyl and propargyl.

As used herein, the term "alkoxy," by itself or as part of another substituent, means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are ($C_1$-$C_3$)alkoxy, particularly ethoxy and methoxy.

As used herein, the terms "carbamyl" or "carbamoyl" means the group —C(=O)NRR', wherein R and R' are independently selected from hydrogen or a hydrocarbyl functional group, or wherein R and R' combined form a heterocycle. Examples of carbamyl groups include: —C(=O)NH$_2$ and —C(=O)N(CH$_3$)$_2$.

As used herein, the term "cyano," by itself or as part of another substituent, means, unless otherwise stated, a —C≡N group.

As used herein, the term "heteroalkyl," by itself or as part of another substituent, means, unless otherwise stated, a stable straight or branched chain alkyl group consisting of the stated number of carbon atoms and one or two heteroatoms selected from the group consisting of oxygen, nitrogen, and sulfur, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$.

As used herein, the terms "halo" or "halogen," by themselves or as part of another substituent, mean, unless otherwise stated, a monovalent fluorine, chlorine, bromine, or iodine atom.

As used herein, the term "nitro," by itself or as part of another substituent, means, unless otherwise stated, a —NO$_2$ group.

As used herein, the term "(C$_x$-C$_y$)perfluoroalkyl," wherein x<y, means an alkyl group with a minimum of x carbon atoms and a maximum of y carbon atoms, wherein all hydrogen atoms are replaced by fluorine atoms. Preferred is —(C$_1$-C$_6$)perfluoroalkyl, more preferred is —(C$_1$-C$_3$)perfluoroalkyl, most preferred is —CF$_3$.

As used herein, the term "aromatic" generally refers to a carbocycle or heterocycle having one or more polyunsaturated rings having aromatic character (i.e. having (4n+2) delocalized π (pi) electrons where n is an integer).

As used herein, the term "aryl," by itself or as part of another substituent, means, unless otherwise stated, a carbocyclic aromatic system containing one or more rings (typically one, two, or three rings) wherein such rings may be attached together in a pendant manner, such as a biphenyl, or may be fused, such as naphthalene. Examples include phenyl; anthracyl; and naphthyl. Preferred are phenyl and naphthyl, most preferred is phenyl.

As used herein, the terms "heterocycle," "heterocyclyl," or "heterocyclic," by itself or as a part of another substituent, means, unless otherwise stated, an unsubstituted or substituted, stable, mono- or multi-cyclic heterocyclic ring system that consists of carbon atoms and at least one heteroatom independently selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure.

As used herein, the terms "heteroaryl" or "heteroaromatic," by itself or as a part of another substituent, means, unless otherwise stated, a heterocycle having aromatic character. Similarly, the term "heteroaryl(C$_1$-C$_3$)alkyl" means a functional group wherein a one to three carbon alkylene chain is attached to a heteroaryl group, e.g., —CH$_2$—CH$_2$-pyridyl. The term "substituted heteroaryl(C$_1$-C$_3$)alkyl" means a heteroaryl(C$_1$-C$_3$)alkyl functional group in which the heteroaryl group is substituted. A polycyclic heteroaryl may include fused rings. Examples include indole, 1H-indazole, 1H-pyrrolo[2,3-b]pyridine, and the like. A polycyclic heteroaryl may include one or more rings that are partially saturated. Examples include indoline, tetrahydroquinoline, and 2,3-dihydrobenzofuryl.

Examples of non-aromatic heterocycles include monocyclic groups such as: aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, piperazine, N-methylpiperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

Examples of heteroaryl groups include: pyridyl, pyrazinyl, pyrimidinyl, particularly 2- and 4-pyrimidinyl, pyridazinyl, thienyl, furyl, pyrrolyl, particularly 2-pyrrolyl, imidazolyl, thiazolyl, oxazolyl, pyrazolyl, particularly 3- and 5-pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl, and 1,3,4-oxadiazolyl.

Polycyclic heterocycles include both aromatic and non-aromatic polycyclic heterocycles. Examples of polycyclic heterocycles include: indolyl, particularly 3-, 4-, 5-, 6-, and 7-indolyl; indolinyl; indazolyl, particularly 1H-indazol-5-yl; quinolyl; tetrahydroquinolyl; isoquinolyl, particularly 1- and 5-isoquinolyl; 1,2,3,4-tetrahydroisoquinolyl; cinnolyl; quinoxalinyl, particularly 2- and 5-quinoxalinyl; quinazolinyl; phthalazinyl; 1,8-naphthyridinyl; 1,4-benzodioxanyl; coumaryl; dihydrocoumaryl; naphthyridinyl, particularly 3,4- and 1,5-naphthyridinyl; benzofuryl, particularly 5-, 6-, and 7-benzofuryl; 2,3-dihydrobenzofuryl; 1,2-benzisoxazolyl; benzothienyl, particularly 3-, 4-, 5-, 6-, and 7-benzothienyl; benzoxazolyl; benzothiazolyl, particularly 2-benzothiazolyl and 5-benzothiazolyl; purinyl; benzimidazolyl, particularly 2-benzimidazolyl; benzotriazolyl; thioxanthinyl; carbazolyl; carbolinyl; acridinyl; pyrrolizidinyl; pyrrolo[2,3-b]pyridinyl, particularly 1H-pyrrolo[2,3-b]pyridine-5-yl; and quinolizidinyl. Particularly preferred are 4-indolyl, 5-indolyl, 6-indolyl, 1H-indazol-5-yl, and 1H-pyrrolo[2,3-b]pyridine-5-yl.

The aforementioned listing of heterocyclyl and heteroaryl moieties is intended to be representative and not limiting.

As used herein, the term "substituted" means, unless otherwise stated, that an atom or group of atoms has replaced hydrogen as the substituent attached to another group. For aryl and heteroaryl groups, the term "substituted" refers, unless otherwise stated, to any level of substitution, namely mono-, di-, tri-, tetra-, or penta-substitution, where such substitution is permitted. The substituents are independently selected, and substitution may be at any chemically accessible position.

As used herein, the term "aryl(C$_1$-C$_3$)alkyl," by itself or as part of another substituent, means, unless otherwise stated, a functional group wherein a (C$_1$-C$_3$)alkylene chain is attached to an aryl group, e.g., —CH$_2$—CH$_2$-phenyl. Examples include aryl(CH$_2$)— and aryl(CH(CH$_3$))—. As used herein, the term "substituted aryl(C$_1$-C$_3$)alkyl," by itself or as part of another substituent, means, unless otherwise stated, means an aryl(C$_1$-C$_3$)alkyl functional group in which the aryl group is substituted. Preferred is substituted aryl(CH$_2$)—. Similarly, as used herein, the term "heterocycle(C$_1$-C$_3$)alkyl," by itself or as part of another substituent, means, unless otherwise stated, a functional group wherein a (C$_1$-C$_3$)alkylene chain is attached to a heterocyclic group, e.g., morpholino-CH$_2$—CH$_2$—. As used herein, the term "substituted heteroaryl($C_1$-$C_3$)alkyl" means a heteroaryl($C_1$-$C_3$)alkyl functional group in which the heteroaryl group is substituted.

Salts of Compounds or Derivatives of the Invention

The compounds of the present invention may take the form of salts. The term "salts" embraces additional salts of free acids or free bases that are compounds of the invention. As used herein, the term "pharmaceutically acceptable salt" refers, unless otherwise stated, to salts that possess toxicity profiles within a range that affords utility in pharmaceutical applications.

Suitable pharmaceutically acceptable acid addition salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from: aliphatic; cycloaliphatic; aromatic; araliphatic; heterocyclic; carboxylic; and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxy ethanesulfonic, p-toluenesulfonic, sulfanilic, cyclohexylaminosulfonic, stearic, alginic, β-hydroxybutyric, salicylic, galactaric, and galacturonic acid. In the present examples of compounds having formulas selected from (Ia), (I-Ha), (IIa), (II-H), (II-Ha), (II-Hb), and (II-Hc), compounds containing pyridine groups, or fused-ring pyridines, such as azaindoles, can be isolated as salts of inorganic acids or strong organic acids, e.g., hydrochloric acid or trifluoroacetic acid. In the present examples of compounds having formulas selected from (Ia), (I-Ha), (IIa), (II-H), (II-Ha), (II-Hb), and (II-Hc), i.e., compounds containing amino groups, said compounds can be isolated as salts of inorganic acids or strong acids, e.g., hydrochloric acid or trifluoroacetic acid.

Suitable pharmaceutically acceptable base addition salts of compounds of the invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl)aminomethane), and procaine.

All of these salts may be prepared by conventional means from the corresponding compound having a formula selected from (Ia), (I-Ha), (IIa), (II-H), (II-Ha), (II-Hb), and (II-Hc), by reacting, for example, the appropriate acid or base with the compound having a formula selected from (Ia), (I-Ha), (IIa), (II-H), (II-Ha), (II-Hb), and (II-Hc). Preferably the salts are in crystalline form, and preferably prepared by crystallization of the sale from a suitable solvent. The person skilled in the art will know how to prepare and select suitable salts forms, for example, as described in P. H. STAHL & C. G. WERMUTH, HANDBOOK OF PHARMACEUTICALS SALTS: PROPERTIES, SELECTION, AND USE (Wiley-VCH 2002), incorporated by reference herein.

Routes of Administration

The compounds may be administered by any route, including but not limited to oral, sublingual, buccal, ocular, pulmonary, rectal, and parenteral administration, or as an oral or nasal spray (e.g., inhalation of nebulized vapors, droplets, or solid particles). Parenteral administration includes, for example, intravenous, intramuscular, intraarterial, intraperitoneal, intranasal, intravaginal, intravesical (e.g., to the bladder), intradermal, transdermal, topical, or subcutaneous administration. Also contemplated within the scope of the invention is the instillation of one or more NR, NAR, NRH, or NARH derivatives, including prodrugs, solvates, or salts thereof, in the body of the patient in a controlled formulation, with systemic or local release of the drug to occur at a later time. For example, injection or infusion of the drug into the liver is contemplated. For example, the drug may be localized in a depot for controlled release to the circulation. The compounds exclude only the parent derivative "NR" itself (I).

The embodiments of the present methods for treating and/or preventing symptoms, diseases, disorders, or conditions associated with, or having etiologies involving, vitamin B3 deficiency and/or that would benefit from increased mitochondrial activity in a mammalian subject, e.g. human, comprising administering or providing a nicotinyl compound (I derivative, II, and/or III) or a derivative, prodrug or salt thereof alone or in combination with a vitamin (IV, V, VI, and/or VII) described herein have not been demonstrated before.

Additionally, the embodiments of the present methods for treating and/or preventing symptoms, diseases, disorders, or conditions associated with, or having etiologies involving, vitamin B3 deficiency and/or that would benefit from increased mitochondrial activity in a mammalian subject address limitations of existing technologies to treat or prevent symptoms, diseases, disorders, or conditions associated with, or having etiologies involving, vitamin B3 deficiency and/or that would benefit from increased mitochondrial activity.

In certain embodiments, the present invention provides methods for treating and/or preventing symptoms, diseases, disorders, or conditions associated with, or having etiologies involving, vitamin B3 deficiency. Exemplary symptoms, diseases, disorders, or conditions associated with, or having etiologies involving, vitamin B3 deficiency that may be treated and/or prevented in accordance with the methods described include indigestion, fatigue, canker sores, vomiting, poor circulation, burning in the mouth, swollen red tongue, and depression. Severe vitamin B3 deficiency can cause a condition known as pellagra, a premature aging condition that is characterized by cracked, scaly skin, dementia, and diarrhea. Other conditions characterized by premature or accelerated aging include Cockayne Syndrome, Neill-Dingwall Syndrome, progeria, and the like.

In certain embodiments, the present invention provides methods for treating and/or preventing symptoms, diseases, disorders, or conditions that would benefit from increased mitochondrial activity. Increased mitochondrial activity refers to increasing activity of the mitochondria while maintaining the overall numbers of mitochondria (e.g., mitochondrial mass), increasing the numbers of mitochondria thereby increasing mitochondrial activity (e.g., by stimulating mitochondrial biogenesis), or combinations thereof. In certain embodiments, symptoms, diseases, disorders, or conditions that would benefit from increased mitochondrial activity include symptoms, diseases, disorders, or conditions associated with mitochondrial dysfunction.

In certain embodiments, methods for treating and/or preventing symptoms, diseases, disorders, or conditions that would benefit from increased mitochondrial activity may comprise identifying a subject suffering from a mitochondrial dysfunction. Methods for diagnosing a mitochondrial dysfunction that may involve molecular genetic, pathologic, and/or biochemical analysis are summarized in Bruce H. Cohen & Deborah R. Gold, *Mitochondrial cytopathy in adults: what we know so far,* 68 CLEVELAND CLINIC J. MED. 625 (2001). One method for diagnosing a mitochondrial dysfunction is the Thor-Byrneier scale (see, e.g., Cohen & Gold 2001; S. Collins et al., *Respiratory Chain Encephalomyopathies: A Diagnostic Classification,* 36 EUROPEAN NEUROLOGY 260 (1996)).

Mitochondria are critical for the survival and proper function of almost all types of eukaryotic cells. Mitochondria in virtually any cell type can have congenital or acquired defects that affect their function. Thus, the clinically significant signs and symptoms of mitochondrial defects affecting respiratory chain function are heterogeneous and variable depending on the distribution of defective mitochondria among cells and the severity of their deficits, and upon physiological demands upon the affected cells. Nondividing tissues with high energy requirements, e.g., nervous tissue, skeletal muscle, and cardiac muscle are particularly susceptible to mitochondrial respiratory chain dysfunction, but any organ system can be affected.

Symptoms, diseases, disorders, and conditions associated with mitochondrial dysfunction include symptoms, diseases, disorders, and conditions in which deficits in mitochondrial respiratory chain activity contribute to the development of pathophysiology of such symptoms, diseases, disorders, or conditions in a mammal. This includes 1) congenital genetic deficiencies in activity of one or more components of the mitochondrial respiratory chain, wherein such deficiencies are caused by a) oxidative damage during aging; b) elevated intracellular calcium; c) exposure of affected cells to nitric oxide; d) hypoxia or ischemia; e) microtubule-associated deficits in axonal transport of mitochondria; or f) expression of mitochondrial uncoupling proteins.

Symptoms, diseases, disorders, or conditions that would benefit from increased mitochondrial activity generally include for example, diseases in which free radical mediated oxidative injury leads to tissue degeneration, diseases in which cells inappropriately undergo apoptosis, and diseases in which cells fail to undergo apoptosis. Exemplary symptoms, diseases, disorders, or conditions that would benefit from increased mitochondrial activity include, for example, AD (Alzheimer's Disease), ADPD (Alzheimer's Disease and Parkinson's Disease), AMDF (Ataxia, Myoclonus and Deafness), auto-immune disease, lupus, lupus erythematosus, SLE (systemic lupus erythematosus), cataracts, cancer, CIPO (Chronic Intestinal Pseudoobstruction with myopathy and Ophthalmoplegia), congenital muscular dystrophy, CPEO (Chronic Progressive External Ophthalmoplegia), DEAF (Maternally inherited DEAFness or aminoglycoside-induced DEAFness), DEMCHO (Dementia and Chorea), diabetes mellitus (Type I or Type II), DID-MOAD (Diabetes Insipidus, Diabetes Mellitus, Optic Atrophy, Deafness), DMDF (Diabetes Mellitus and Deafness), dystonia, Exercise Intolerance, ESOC (Epilepsy, Strokes, Optic atrophy, and Cognitive decline), FBSN (Familial Bilateral Striatal Necrosis), FICP (Fatal Infantile Cardiomyopathy Plus, a MELAS-associated cardiomyopathy), GER (Gastrointestinal Reflux), HD (Huntington's Disease), KSS (Kearns Sayre Syndrome), "later-onset" myopathy, LDYT (Leber's hereditary optic neuropathy and DYsTonia), Leigh's Syndrome, LHON (Leber Hereditary Optic Neuropathy), LIMM (Lethal Infantile Mitochondrial Myopathy), MDM (Myopathy and Diabetes Mellitus), MELAS (Mitochondrial Encephalomyopathy, Lactic Acidosis, and Stroke-like episodes), MEPR (Myoclonic Epilepsy and Psychomotor Regression), MERME (MERRF/MELAS overlap disease), MERRF (Myoclonic Epilepsy and Ragged Red Muscle Fibers), MHCM (Maternally Inherited Hypertrophic CardioMyopathy), MICM (Maternally Inherited Cardiomyopathy), MILS (Maternally Inherited Leigh Syndrome), Mitochondrial Encephalocardiomyopathy, Mitochondrial Encephalomyopathy, MM (Mitochondrial Myopathy), MMC (Maternal Myopathy and Cardiomyopathy), MNGIE (Myopathy and external ophthalmoplegia, Neuropathy, Gastro-Intestinal, Encephalopathy), Multisystem Mitochondrial Disorder (myopathy, encephalopathy, blindness, hearing loss, peripheral neuropathy), NARP (Neurogenic muscle weakness, Ataxia, and Retinitis Pigmentosa; alternate phenotype at this locus is reported as Leigh Disease), PD (Parkinson's Disease), Pearson's Syndrome, PEM (Progressive Encephalopathy), PEO (Progressive External Ophthalmoplegia), PME (Progressive Myoclonus Epilepsy), PMPS (Pearson Marrow-Pancreas Syndrome), psoriasis, RTT (Rett Syndrome), schizophrenia, SIDS (Sudden Infant Death Syndrome), SNHL (Sensorineural Hearing Loss), Varied Familial Presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), or Wolfram syndrome.

Other symptoms, diseases, disorders, and conditions that would benefit from increased mitochondrial activity include, for example, Friedreich's ataxia and other ataxias, amyotrophic lateral sclerosis (ALS) and other motor neuron diseases, macular degeneration, epilepsy, Alpers syndrome, Multiple mitochondrial DNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, Refractory epilepsy with declines during infection, Asperger syndrome with declines during infection, Autism with declines during infection, Attention deficit hyperactivity disorder (ADHD), Cerebral palsy with declines during infection, Dyslexia with declines during infection, materially inherited thrombocytopenia and leukemia syndrome, MARIAHS syndrome (Mitochondrial ataxia, recurrent infections, aphasia, hypouricemia/hypomyelination, seizures, and dicarboxylic aciduria), ND6 dystonia, Cyclic vomiting syndrome with declines during infection, 3-Hydroxy isobutyric aciduria with lactic acidemia, Diabetes mellitus with lactic acidemia, Uridine responsive neurologic syndrome (URNS), Dilated cardiomyopathy, Splenic Lymphoma, or Renal Tubular Acidosis/Diabetes/Ataxis syndrome.

In other embodiments, the present invention provides methods for treating a mammal (e.g., human) suffering from mitochondrial disorders arising from, but not limited to, Post-traumatic head injury and cerebral edema, Stroke (invention methods useful for treating or preventing reperfusion injury), Lewy body dementia, Hepatorenal syndrome, Acute liver failure, NASH (non-alcoholic steatohepatitis), Anti-metastasis/prodifferentiation therapy of cancer, Idiopathic congestive heart failure, Atrial fibrillation (non-valvular), Wolff-Parkinson-White Syndrome, Idiopathic heart block, Prevention of reperfusion injury in acute myocardial infarctions, Familial migraines, Irritable bowel syndrome, Secondary prevention of non-Q wave myocardial infarctions, Premenstrual syndrome, Prevention of renal failure in hepatorenal syndrome, Anti-phospholipid antibody syndrome, Eclampsia/pre-eclampsia, Oopause infertility, Ischemic heart disease/Angina, and Shy-Drager and unclassified dysautonomia syndromes.

In still another embodiment, there are provided methods for the treatment of mitochondrial disorders associated with pharmacological drug-related side effects. Types of pharmaceutical agents that are associated with mitochondrial disorders include reverse transcriptase inhibitors, protease inhibitors, inhibitors of DHOD, and the like. Examples of reverse transcriptase inhibitors include, for example, Azidothymidine (AZT), Stavudine (D4T), Zalcitabine (ddC), Didanosine (DDI), Fluoroiodoarauracil (FIAU), Lamivudine (3TC), Abacavir, and the like. Examples of protease inhibitors include, for example, Ritonavir, Indinavir, Saquinavir, Nelfinavir, and the like. Examples of inhibitors of dihydroorotate dehydrogenase (DHOD) include, for example, Leflunomide, Brequinar, and the like.

Reverse transcriptase inhibitors not only inhibit reverse transcriptase but also polymerase gamma, which is required for mitochondrial function. Inhibition of polymerase gamma activity (e.g., with a reverse transcriptase inhibitor) therefore leads to mitochondrial dysfunction and/or a reduced mitochondrial mass, which manifests itself in patients as hyperlactatemia. This type of condition may benefit from an increase in the number of mitochondria and/or an improvement in mitochondrial function.

Common symptoms of mitochondrial diseases include cardiomyopathy, muscle weakness and atrophy, developmental delays (involving motor, language, cognitive, or executive function), ataxia, epilepsy, renal tubular acidosis, peripheral neuropathy, optic neuropathy, autonomic neuropathy, neurogenic bowel dysfunction, sensorineural deafness, neurogenic bladder dysfunction, dilating cardiomyopathy, migraine, hepatic failure, lactic acidemia, and diabetes mellitus.

In exemplary embodiments, the invention provides methods for treating diseases or disorders that would benefit from increased mitochondrial activity by administering to a mammal (e.g., human) a therapeutically effective amount of at least one nicotinyl compound (I derivative, II, and/or III) or a derivative, prodrug or salt thereof alone or in combination with at least one vitamin (IV, V, VI, VII). Exemplary diseases or disorders include, for example, neuromuscular disorders (e.g., Friedreich's Ataxia, muscular dystrophy, multiple sclerosis, etc.), disorders of neuronal instability (e.g., seizure disorders, migraine, etc.), developmental delay, neurodegenerative disorders (e.g., Alzheimer's Disease, Parkinson's Disease, amyotrophic lateral sclerosis, etc.), ischemia, renal tubular acidosis, age-related neurodegeneration and cognitive decline, chemotherapy fatigue, age-related or chemotherapy-induced menopause or irregularities of menstrual cycling or ovulation, mitochondrial myopathies, mitochondrial damage (e.g., calcium accumulation, excitotoxicity, nitric oxide exposure, hypoxia, etc.), and mitochondrial deregulation.

A gene defect underlying Friedreich's Ataxia (FA), the most common hereditary ataxia, was recently identified and is designated "frataxin." In FA, after a period of normal development, deficits in coordination develop that progress to paralysis and death, typically between the ages of 30 and 40. The tissues affected most severely are the spinal cord, peripheral nerves, myocardium, and pancreas. Patients typically lose motor control and are confined to wheel chairs, and are commonly afflicted with heart failure and diabetes. The genetic basis for FA involves GAA trinucleotide repeats in an intron region of the gene encoding frataxin. The presence of these repeats results in reduced transcription and expression of the gene. Frataxin is involved in regulation of mitochondrial iron content. When cellular frataxin content is subnormal, excess iron accumulates in mitochondria, promoting oxidative damage and consequent mitochondrial degeneration and dysfunction. When intermediate numbers of GAA repeats are present in the frataxin gene intron, the severe clinical phenotype of ataxia may not develop. However, these intermediate-length trinucleotide extensions are found in 25 to 30% of patients with non-insulin dependent diabetes mellitus, compared to about 5% of the nondiabetic population. In certain embodiments, nicotinyl compounds (I derivative, II, and/or III) or derivatives, prodrugs or salts thereof alone or in combination with vitamins (IV, V, VI, and/or VII) may be used for treating mammals (e.g., human) with disorders related to deficiencies or defects in frataxin, including Friedreich's Ataxia, myocardial dysfunction, diabetes mellitus, and complications of diabetes-like peripheral neuropathy.

Muscular dystrophy refers to a family of diseases involving deterioration of neuromuscular structure and function, often resulting in atrophy of skeletal muscle and myocardial dysfunction. In the case of Duchenne muscular dystrophy, mutations or deficits in a specific protein, dystrophin, are implicated in its etiology. Mice with their dystrophin genes inactivated display some characteristics of muscular dystrophy, and have an approximately 50% deficit in mitochondrial respiratory chain activity. A final common pathway for neuromuscular degeneration, in most cases, is calcium-mediated impairment of mitochondrial function. In certain embodiments, nicotinyl compounds (I derivative, II, and/or III) or derivatives, prodrugs or salts thereof alone or in combination with vitamins (IV, V, VI, and/or VII) may be used for reducing the rate of decline in muscular functional capacities and for improving muscular functional status in mammals (e.g., human) with muscular dystrophy.

Epilepsy is often present in patients with mitochondrial cytopathies, involving a range of seizure severity and frequency, e.g., absence, tonic, atonic, myoclonic, and status epilepticus, occurring in isolated episodes or many times daily. In certain embodiments, nicotinyl compounds (I derivative, II, and/or III) or derivatives, prodrugs or salts thereof alone or in combination with vitamins (IV, V, VI, and/or VII) may be used for treating mammals (e.g., human) with seizures secondary to mitochondrial dysfunction, including reducing frequency and severity of seizure activity.

Delays in neurological or neuropsychological development are often found in children with mitochondrial diseases. Development and remodeling of neural connections requires intensive biosynthetic activity, particularly involving synthesis of neuronal membranes and myelin, both of which require pyrimidine nucleotides as cofactors. Uridine nucleotides are involved in activation and transfer of sugars to glycolipids and glycoproteins. Cytidine nucleotides are derived from uridine nucleotides, and are crucial for synthesis of major membrane phospholipid constituents like phosphatidylcholine, which receives its choline moiety from cytidine diphosphocholine. In the case of mitochondrial dysfunction (due to either mitochondrial DNA defects or any of the acquired or conditional deficits like exicitotoxic or nitric oxide-mediated mitochondrial dysfunction) or other conditions resulting in impaired pyrimidine synthesis, cell proliferation and axonal extension are impaired at crucial stages in development of neuronal interconnections and circuits, resulting in delayed or arrested development of neuropsychological functions like language, motor, social, executive function, and cognitive skills. In autism, for example, magnetic resonance spectroscopy measurements of cerebral phosphate compounds indicate that there is global undersynthesis of membranes and membrane precursors indicated by reduced levels of uridine diphosphosugars, and cytidine nucleotide derivatives involved in membrane synthesis. Disorders characterized by developmental delay include Rett's Syndrome, pervasive developmental delay (or PDD-NOS "pervasive developmental delay not otherwise specified" to distinguish it from specific subcategories like autism), autism, Asperger's Syndrome, and Attention Deficit/Hyperactivity Disorder (ADHD), which is becoming recognized as a delay or lag in development of neural circuitry underlying executive functions. In certain embodiments, nicotinyl compounds (I derivative, II, and/or III) or derivatives, prodrugs or salts thereof alone or in combination with vitamins (IV, V, VI, and/or VII) may be useful for treating mammals (e.g., human) with neurodevelopmental delays (e.g., involving motor, language, executive function, and cognitive skills), or other delays or arrests of neurological and neuropsychological development in the nervous system and somatic development in non-neural tissues like muscle and endocrine glands.

Oxygen deficiency results in both direct inhibition of mitochondrial respiratory chain activity by depriving cells of a terminal electron acceptor for Cytochrome c reoxidation at Complex IV, and indirectly, especially in the nervous system, via secondary post-anoxic excitotoxicity and nitric oxide formation. In conditions like cerebral anoxia, angina or sickle cell anemia crises, tissues are relatively hypoxic. In such cases, compounds that increase mitochondrial activity provide protection of affected tissues from deleterious effects of hypoxia, attenuate secondary delayed cell death, and accelerate recovery from hypoxic tissue stress and injury. In certain embodiments, nicotinyl compounds (I derivative, II, and/or III) or derivatives, prodrugs or salts thereof alone or in combination with vitamins (IV, V, VI, and/or VII) may be useful for treating and/or preventing delayed cell death (apoptosis in regions like the hippocampus or cortex occurring about 2 to 5 days after an episode of cerebral ischemia) after ischemic or hypoxic insult to the brain.

Acidosis due to renal dysfunction is often observed in patients with mitochondrial disease, whether the underlying respiratory chain dysfunction is congenital or induced by ischemia or cytotoxic agents like cisplatin. Renal tubular acidosis often requires administration of exogenous sodium bicarbonate to maintain blood and tissue pH. In certain embodiments, nicotinyl compounds (I derivative, II, and/or III) or derivatives, prodrugs or salts thereof alone or in combination with vitamins (IV, V, VI, and/or VII) may be useful for treating and/or preventing renal tubular acidosis and other forms of renal dysfunction caused by mitochondrial respiratory chain deficits.

Mitochondrial DNA damage is more extensive and persists longer than nuclear DNA damage in cells subjected to oxidative stress or cancer chemotherapy agents like cisplatin due to both greater vulnerability and less efficient repair of mitochondrial DNA. Although mitochondrial DNA may be more sensitive to damage than nuclear DNA, it is relatively resistant, in some situations, to mutagenesis by chemical carcinogens. This is because mitochondria respond to some types of mitochondrial DNA damage by destroying their defective genomes rather than attempting to repair them. This results in global mitochondrial dysfunction for a period after cytotoxic chemotherapy. Clinical use of chemotherapy agents like cisplatin, mitomycin, and cytoxan is often accompanied by debilitating "chemotherapy fatigue," prolonged periods of weakness and exercise intolerance that may persist even after recovery from hematologic and gastrointestinal toxicities of such agents. In certain embodiments, nicotinyl compounds (I derivative, II, and/or III) or derivatives, prodrugs or salts thereof alone or in combination with vitamins (IV, V, VI, and/or VII) may be useful for treatment and/or prevention of side effects of cancer chemotherapy related to mitochondrial dysfunction.

In certain embodiments, nicotinyl compounds (I derivative, II, and/or III) or derivatives, prodrugs or salts thereof alone or in combination with vitamins (IV, V, VI, and/or VII) may be useful for treatment and/or prevention of mitochondrial myopathies. Mitochondrial myopathies range from mild, slowly progressive weakness of the extraocular muscles to severe, fatal infantile myopathies and multisystem encephalomyopathies. Some syndromes have been defined, with some overlap between them. Established syndromes affecting muscle include progressive external ophthalmoplegia, the Kearns-Sayre syndrome (with ophthalmoplegia, pigmentary retinopathy, cardiac conduction defects, cerebellar ataxia, and sensorineural deafness), the MELAS syndrome (mitochondrial encephalomyopathy, lactic acidosis, and stroke-like episodes), the MERFF syndrome (myoclonic epilepsy and ragged red fibers), limb-girdle distribution weakness, and infantile myopathy (benign or severe and fatal). Muscle biopsy specimens stained with modified Gomori's trichrome stain show ragged red fibers due to excessive accumulation of mitochondria. Biochemical defects in substrate transport and utilization, the Krebs cycle, oxidative phosphorylation, or the respiratory chain are detectable. Numerous mitochondrial DNA point mutations and deletions have been described, transmitted in a maternal, nonmendlian inheritance pattern. Mutations in nuclear-encoded mitochondrial enzymes occur.

In certain embodiments, nicotinyl compounds (I derivative, II, and/or III) or derivatives, prodrugs or salts thereof alone or in combination with vitamins (IV, V, VI, and/or VII) may be useful for treating patients suffering from toxic damage to mitochondria, such as, toxic damage due to calcium accumulation, excitotoxicity, nitric oxide exposure, drug induced toxic damage, or hypoxia.

A fundamental mechanism of cell injury, especially in excitable tissues, involves excessive calcium entry into cells, as a result of either leakage through the plasma membrane or defects in intracellular calcium handling mechanisms. Mitochondria are major sites of calcium sequestration, and preferentially utilize energy from the respiratory chain for taking up calcium rather than for ATP synthesis, which results in a downward spiral of mitochondrial failure, because calcium uptake into mitochondria results in diminished capabilities for energy transduction.

Excessive stimulation of neurons with excitatory amino acids is a common mechanism of cell death or injury in the central nervous system. Activation of glutamate receptors, especially of the subtype designated NMDA receptors, results in mitochondrial dysfunction, in part through elevation of intracellular calcium during excitotoxic stimulation. Conversely, deficits in mitochondrial respiration and oxidative phosphorylation sensitizes cells to excitotoxic stimuli, resulting in cell death or injury during exposure to levels of excitotoxic neurotransmitters or toxins that would be innocuous to normal cells.

Nitric oxide (about 1 micromolar) inhibits cytochrome oxidase (Complex IV) and thereby inhibits mitochondrial respiration; moreover, prolonged exposure to nitric oxide (NO) irreversibly reduces Complex I activity. Physiological or pathophysiological concentrations of NO thereby inhibit pyrimidine biosynthesis. Nitric oxide is implicated in a variety of neurodegenerative disorders including inflammatory and autoimmune diseases of the central nervous system, and is involved in mediation of excitotoxic and post-hypoxic damage to neurons.

Oxygen is the terminal electron acceptor in the respiratory chain. Oxygen deficiency impairs electron transport chain activity, resulting in diminished pyrimidine synthesis as well as diminished ATP synthesis via oxidative phosphorylation. Human cells proliferate and retain viability under virtually anaerobic conditions if provided with uridine and pyruvate (or a similarly effective agent for oxidizing NADH to optimize glycolytic ATP production).

In certain embodiments, nicotinyl compounds (I derivative, II, and/or III) or derivatives, prodrugs or salts thereof alone or in combination with vitamins (IV, V, VI, and/or VII) may be useful for treating and/or preventing diseases or disorders associated with mitochondrial deregulation.

Transcription of mitochondrial DNA encoding respiratory chain components requires nuclear factors. In neuronal axons, mitochondria must shuttle back and forth to the nucleus in order to maintain respiratory chain activity. If axonal transport is impaired by hypoxia or by drugs like taxol that affect microtubule stability, mitochondria distant from the nucleus undergo loss of cytochrome oxidase activity. Accordingly, treatment with nicotinyl compounds (I derivative, II, and/or III) or derivatives, prodrugs or salts thereof alone or in combination with vitamins (IV, V, VI, and/or VII) may be useful for promoting nuclear-mitochondrial interactions.

Mitochondria are the primary source of free radicals and reactive oxygen species, due to spillover from the mitochondrial respiratory chain, especially when defects in one or more respiratory chain components impairs orderly transfer of electrons from metabolic intermediates to molecular oxygen. To reduce oxidative damage, cells can compensate by expressing mitochondrial uncoupling proteins (UCP), of which several have been identified. UCP-2 is transcribed in response to oxidative damage, inflammatory cytokines, or excess lipid loads, e.g., fatty liver and steatohepatitis. UCPs reduce spillover of reactive oxygen species from mitochondria by discharging proton gradients across the mitochondrial inner membrane, in effect wasting energy produced by metabolism and rendering cells vulnerable to energy stress as a trade-off for reduced oxidative injury.

Salts of Nicotinyl Compounds (I derivative, II, and III), or Reduced Derivatives thereof. According to the Present Invention The methods of using nicotinyl compounds (I derivative, II, and III) of the present invention may take the form of salts. The term "salts" embraces addition salts of free acids or free bases that are nicotinyl compounds (I derivative, II, and III) or derivatives thereof in the methods of the present invention. The term "pharmaceutically acceptable salt" refers to salts that possess toxicity profiles within a range that affords utility in pharmaceutical applications.

Suitable pharmaceutically acceptable acid addition salts may be prepared from an inorganic acid or from an organic acid. Examples of inorganic acids include hydrochloric, hydrobromic, hydroiodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoroacetic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. In the present examples of uses of nicotinyl compounds (I derivative, II, and III) or derivatives thereof, i.e., compounds containing amino groups and pyridinium groups, said compounds can be isolated as salts of inorganic acids or strong organic acids, e.g., hydrochloric acid or trifluoroacetic acid.

Suitable pharmaceutically acceptable base additional salts of nicotinyl compounds of the methods of the present invention include, for example, metallic salts including alkali metal, alkaline earth metal, and transition metal salts such as, for example, calcium, magnesium, potassium, sodium, and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine), tromethamine (tris(hydroxymethyl)aminomethane), and procaine.

Optionally wherein a basic counterion, or anion, is present, said basic counterion or anion is selected form the group consisting of fluoride, chloride, bromide, iodide, formate, acetate, ascorbate, benzoate, carbonate, citrate, carbamate, formate, gluconate, lactate, methyl bromide, methyl sulfate, nitrate, phosphate, diphosphate, succinate, sulfate, trifluoromethanesulfonate, and trifluoroacetate; and optionally the basic counterion, or anion, is an internal salt;

optionally the basic counterion, or anion, is an anion of a substituted or unsubstituted carboxylic acid selected from a monocarboxylic acid, a dicarboxylic acid, or a polycarboxylic acid;

optionally the basic counterion, or anion, is an anion of a substituted monocarboxylic acid, further optionally an anion of a substituted propanoic acid (propanoate or propionate), or an anion of a substituted acetic acid (acetate), or an anion of a hydroxyl-propanoic acid, or an anion of 2-hydroxypropanoic acid (being lactic acid; the anion of lactic acid being lactate), or a trihaloacetate selected from trichloroacetate, tribromoacetate, and trifluoroacetate; and optionally the basic counterion, or anion, is an anion of an unsubstituted monocarboxylic acid selected from formic acid, acetic acid, propionic acid, or butyric acid, being formate, acetate, propionate, and butyrate, respectively; and optionally the basic counterion, or anion, is an anion of a substituted or unsubstituted amino acid, i.e. amino-monocarboxylic acid or an amino-dicarboxylic acid, optionally selected from glutamic acid and aspartic acid, being glutamate and aspartate, respectively; and optionally the basic counterion, or anion, is an anion of ascorbic acid, being ascorbate; and optionally the basic counterion, or anion, is a halide selected from fluoride, chloride, bromide, or iodide; and optionally the basic counterion, or anion, is an anion of a substituted or unsubstituted sulfonate, further optionally a trihalomethanesulfonate selected from trifluoromethanesulfonate, tribromomethanesulfonate, or trichloromethanesulfonate; and optionally the basic counterion, or anion, is an anion of a substituted or unsubstituted carbonate, further optionally hydrogen carbonate.

All these salts may be prepared by conventional means from the corresponding nicotinyl compounds (I derivative, II, and III) or derivatives thereof, by reacting, for example, the appropriate acid or base with the nicotinyl compounds (I derivative, II, and III) or derivatives thereof. Preferably, the salts are in crystalline form, or alternatively in dried or freeze-dried form. The person skilled in the art will know how to prepare and select suitable forms, for example, as described in P. H. STAHL & C. G. WERMUTH, HANDBOOK OF PHARMACEUTICAL SALTS: PROPERTIES, SELECTION, AND USE (Wiley-VCH 2002).

Delivery and Administration Systems of the Present Invention

The methods described herein may comprise administering daily, or every other day, or once a week, a high dose of nicotinyl compounds (I derivative, II, and/or III) or derivatives, prodrugs or salts thereof alone or in combination with vitamins (IV, V, VI, and/or VII), e.g., in the form of a pill, to a subject. In embodiments where the high dose of nicotinyl compounds (I derivative, II, and/or III) or derivatives, prodrugs or salts thereof alone or in combination with vitamins (IV, V, VI, and/or VII) is administered daily to the subject, the nicotinyl compounds (I derivative, II, and/or III) or derivatives, prodrugs or salts thereof alone or in combination with vitamins (IV, V, VI, and/or VII) may be administered once a day. In other embodiments, it is administered twice or three times a day.

In some embodiments, the high dose of nicotinyl compounds (I derivative, II, and/or III) or derivatives, prodrugs or salts thereof alone or in combination with vitamins (IV, V, VI, and/or VII) is administered in a sustained release formulation, e.g., by embedding or encapsulating the nicotinyl compounds (I derivative, II, and/or III) or derivatives, prodrugs or salts thereof alone or in combination with vitamins (IV, V, VI, and/or VII) into neoparticles for delivery over a period of at least 12 hours, to a subject. In embodiments where the nicotinyl compounds (I derivative, II, and/or III) or derivatives, prodrugs or salts thereof alone or in combination with vitamins (IV, V, VI, and/or VII) is administered to a subject in a sustained release formulation, a high dose of the nicotinyl compounds (I derivative, II, and/or III) or derivatives, prodrugs or salts thereof alone or in combination with vitamins (IV, V, VI, and/or VII) may be administered for sustained delivery over a period of, for example, at least about 12, 15, 18, 24, or 36 hours, or longer. In other embodiments, it is administered for a sustained delivery over a period of one or more days. In yet other embodiments, it is administered for a sustained delivery over a period of one or more weeks. In another embodiment, an implantable device can be used to carry out sustained release or time release in a specific tissue, such as in the ear or eye.

In certain embodiments, the nicotinyl compounds (I derivative, II, and/or III) or derivatives, prodrugs or salts thereof alone or in combination with vitamins (IV, V, VI, and/or VII) are administered in a nutraceutical formulation. A "nutraceutical" is any functional food (including beverages) that provides an additional benefit other than its nutritional benefit. In a preferred embodiment, a nutraceutical is provided and contains from about 0.1% to about 99%, or from about 0.1% to about 10% of nicotinyl compounds (I derivative, II, and/or III) or derivatives, prodrugs or salts thereof alone or in combination with vitamins (IV, V, VI, and/or VII) by weight. In preferred embodiments, a high dose as described herein of nicotinyl compounds (I derivative, II, and/or III) or derivatives, prodrugs or salts thereof alone or in combination with vitamins (IV, V, VI, and/or VII) is administered in a single serving of a food or beverage. In a preferred formulation, a single dosage form is provided (e.g., an 8 fluid ounce serving of a beverage such as water, flavored water, or fruit juice) that contains a quantity of nicotinyl compounds (I derivative, II, and/or III) or derivatives, prodrugs or salts thereof alone or in combination with vitamins (IV, V, VI, and/or VII) that has a physiological effect equal to or greater than the physiological effect of 25 mg total of nicotinyl compounds (I derivative, II, and/or III) or derivatives, prodrugs or salts thereof alone or in combination with vitamins (IV, V, VI, and/or VII). In other embodiments, a single dosage form is provided that contains a quantity of total nicotinyl compounds (I derivative, II, and/or III) or derivatives, prodrugs or salts thereof alone or in combination with vitamins (IV, V, VI, and/or VII) that has a physiological effect equal to or greater than the physiological effect of about 10, 15, 20, 25, 50, 60, 75, 80, 100, 150, 200, or more mg nicotinyl compounds (I derivative, II, and/or III) or derivatives, prodrugs or salts thereof alone or in combination with vitamins (IV, V, VI, and/or VII) per 8 fluid ounces. In other preferred embodiments, a single dosage form is provided (e.g., a serving of food such as a nutrition bar) that contains a total quantity of nicotinyl compounds (I derivative, II, and/or III) or derivatives, prodrugs or salts thereof alone or in combination with vitamins (IV, V, VI, and/or VII) that as a physiological effect equal to or greater than the physiological effect of 100 mg nicotinyl compounds (I derivative, II, and/or III) or derivatives, prodrugs or salts thereof alone or in combination with vitamins (IV, V, VI, and/or VII). In some embodiments, the food supplies 100 to 500 kcal per serving. In other embodiments, a single dosage form is provided that contains a total quantity of nicotinyl compounds (I derivative, II, and/or III) or derivatives, prodrugs or salts thereof alone or in combination with vitamins (IV, V, VI, and/or VII) that has a physiological effect equal to or greater than the physiological effect of 20, 50, 60, 75, 80, 100, 150, 200, 250, or more, mg nicotinyl compounds (I derivative, II, and/or III) or derivatives, prodrugs or salts thereof alone or in combination with vitamins (IV, V, VI, and/or VII) per 100 to 500 kcal. The phrase "total quantity of nicotinyl compounds (I derivative, II, and/or III) or derivatives, prodrugs or salts thereof alone or in combination with vitamins (IV, V, VI, and/or VII)" refers to the total amount of nicotinyl compounds (I derivative, II, and/or III) or derivatives, prodrugs or salts thereof alone or in combination with vitamins (IV, V, VI, and/or VII) present in the single dosage form.

In various embodiments, a nutraceutical comprising nicotinyl compounds (I derivative, II, and/or III) or derivatives, prodrugs or salts thereof alone or in combination with vitamins (IV, V, VI, and/or VII) may be any variety of food or drink. For example, nutraceuticals may include drinks such as nutritional drinks, diet drinks (e.g., Slimfast™ Boost™, and the like) as well as sports, herbal, and other fortified beverages. Additionally, nutraceuticals may include foods intended for human or animal consumption such as baked goods, for example, bread, wafers, cookies, crackers, pretzels, pizza, and rolls, ready-to-eat breakfast cereals, hot cereals, pasta products, snacks such as fruit snacks, salty snacks, grain snacks, nutrition bars, and microwave popcorn, dairy products such as yogurt, cheese, and ice cream, sweet goods such as hard candy, soft candy, and chocolate, beverages, animal feed, pet foods such as dog food and cat food, aqua-culture foods such as fish food and shrimp feed, and special purpose foods such as baby food, infant formulas, hospital food, medical food, sports food, performance food or nutritional bars, or fortified foods, food preblends or mixes for home or food service use, such as preblends for soups or gravy, dessert mixes, dinner mixes, baking mixes such as bread mixes, and cake mixes, and baking flower. In certain embodiments, the food or beverage does not include one or more of grapes, mulberries, blueberries, raspberries, peanuts, milk, yeast, or extracts thereof.

In certain embodiments, methods for delivering the nicotinyl compounds (I derivative, II, and/or III) or derivatives, prodrugs or salts thereof alone or in combination with vitamins (IV, V, VI, and/or VII) of the present invention to a mammal (e.g., human) in need thereof, and methods of treating and/or preventing symptoms, diseases, disorders, or conditions associated with, or having etiologies involving, vitamin B3 deficiency and/or that would benefit from increased mitochondrial activity in a mammal (e.g., human) comprise delivering or administering an infant formula.

Useful compositions may include one or more compounds selected from nicotinyl compounds (I derivative, II, and/or III) or derivatives, prodrugs or salts thereof alone or in combination with vitamins (IV, V, VI, and/or VII)

Oral formulations of NR (I) derivatives, or NAR (II) and/or NMN (III), or derivatives thereof, are contemplated. Useful therapeutic dosages of one or more nicotinyl compounds (I derivative, II, and/or III) or derivatives, prodrugs or salts thereof can range, but are not limited to, from about 0.1 mg to about 10,000 mg in a human individual. Another suitable dose range is from about 100 mg to about 1000 mg. Another suitable dose range is from about 5 mg to about 500 mg. Another suitable dose range is from about 50 mg to about 500 mg. Nicotinyl compounds (I derivative, II, and/or III) or derivatives, prodrugs or salts thereof may be formulated orally or topically as a pharmaceutical or nutraceutical composition, including a pharmaceutically or nutraceutically acceptable carrier, respectively. In one embodiment of a pharmaceutical composition containing one or more nicotinyl compounds (I derivative, II, and/or III) or derivatives, prodrugs or salts thereof, a suitable level of one or more compounds may range from about 0.01% by weight to about 50% by weight, based on the total weight of the composition. In another embodiment of a pharmaceutical composition containing nicotinyl compounds (I derivative, II, and/or III) or derivatives, prodrugs or salts thereof, a suitable level of one or more compounds may range from about 0.1% by weight to about 10% by weight, based on the total weight of the composition.

Examples of suitable fat sources typically include high oleic safflower oil, soy oil, fractionated coconut oil (medium chain triglycerides, MCT oil), high oleic sunflower oil, corn oil, canola oil, coconut, palm and palm kernel oils, marine oil, cottonseed oil, walnut oil, wheat germ oil, sesame oil, cod liver oil, and peanut oil. Any single fat listed above, or any combination thereof, as appropriate, may be utilized. Other suitable fats will be readily apparent to those skilled in the art.

The nutritional formulas used in the methods of the present invention may be packaged and sealed in single or multi-use containers, and then stored under ambient conditions for up to about 36 months or longer, more typically from about 12 to about 24 months. For multi-use containers, these packages can be opened and then covered for repeated use by the ultimate user, provided that the covered package is then stored under ambient conditions (e.g., avoid extreme temperatures) and the contents used within about one month or so.

Compositions for oral formulations useful for delivering a dietary supplement composition comprising nicotinyl compounds (I derivative, II, and/or III) or derivatives, prodrugs or salts thereof alone or in combination with vitamins (IV, V, VI, and/or VII) that are palatable to mammals (e.g., humans) are known in the art. The infant dietary supplement composition useful for delivering comprising nicotinyl compounds (I derivative, II, and/or III) or derivatives, prodrugs or salts thereof alone or in combination with vitamins (IV, V, VI, and/or VII) can be orally administered, for example, with an inert diluents or with an assimilable edible carrier, or it can be enclosed in hard or soft shell gelatin capsules, or it can be compressed into tablets, or it can be incorporated directly with the food of the diet. For oral administration, the dietary composition comprising nicotinyl compounds (I derivative, II, and/or III) or derivatives, prodrugs or salts thereof alone or in combination with vitamins (IV, V, VI, and/or VII) may be incorporated with an excipient and used in the form of ingestible tablets, buccal tablets, troches, capsules, elixirs, suspensions, syrups, wafers, and the like. The tablets, troches, pills, capsules, and the like can also contain the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; and a sweetening agent such as sucrose, lactose, or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the active compound, sucrose as a sweetening agent, methyl and propylparabens as preservatives, a dye, and flavoring such as cherry or orange flavor. Oil-in-water emulsions may be better suited for oral use in infants or children because these are water-miscible, and thus their oiliness is masked. Such emulsions are well known in the pharmaceutical sciences.

Example A

Materials and Methods: Hela Cell Culture

Hela cells (passages 5-9) were grown in cell culture medium DMEM with 10% serum and were seeded in 6-well plates with a density of $3 \times 10^5$ cells per well containing 1 ml of culture medium overnight. The wells were aspirated, washed with PBS and 2 mL of fresh cell culture media was added. To each well was added 2 μL of a freshly prepared 100 mM solution of the corresponding $NAD^+$ precursor (a nicotinyl riboside test compound) in water to give a final concentration of 100 μM per well and then incubated for 24 h at 37° C. The media was aspirated and the wells washed with PBS, and for each condition $1 \times 10^5$ cells were isolated and analyzed using an ENZYCHROM™ NAD+/NADH ASSAY KIT (E2ND-100) following the manufacturer protocol (BioAssay Systems, Hayward, Calif.). This standard assay provides a quantitative colorimetric determination of NAD+/NADH at 565 nm.

TABLE 1

|  | NAD % vs control | STDEV |
| --- | --- | --- |
| control | 100.0 | 0.0 |
| NR | 141.0 | 18.2 |
| NR TA | 199.3 | 180.8 |
| NRH | 557.1 | 274.2 |
| NRH TA | 146.5 | 35.1 |
| NAR | 295.3 | 259.2 |
| NAR TA | 172.6 | 75.8 |
| NARH | 147.0 | 81.4 |
| NARH TA | 177.9 | 76.7 |
| cyclic | 178.0 | 49.9 |

In Table 1, the test compounds are as defined above, while the term "cyclic" refers to 2',3'-diacetyl-5'-nicotinoyl ribolactone, which is a precursor of 1-(2',3'-diacetyl-beta-D-ribofuranosyl)-nicotinic acid upon lactone ring opening; further esterase hydrolysis provides NAR. Another useful cyclic derivative is the reduced analogue 2',3'-diacetyl-5'-(1,4-dihydronicotinoyl) ribolactone, which is a precursor of 1-(2',3'-diacetyl-beta-D-ribofuranosyl)-1,4,-dihydronicotinic acid upon lactone ring opening; further esterase hydrolysis provides NARH.

Results and Discussion

As shown in Table 1, each of the nicotinyl derivatives demonstrated a profound and reproducible increase compared to control (NAD content in cells measured in the absence of treatment compound).

Figure 8:
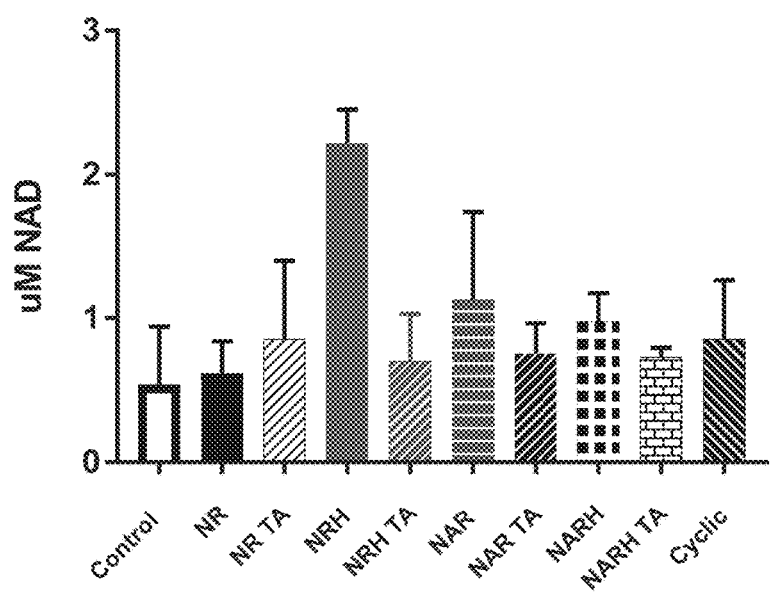
FIG. 8 depicts in another embodiment cultured Hela cells supplemented with an $NAD^+$ precursor (nicotinyl riboside test compound) for 24 hours, versus control.
Figure 9:
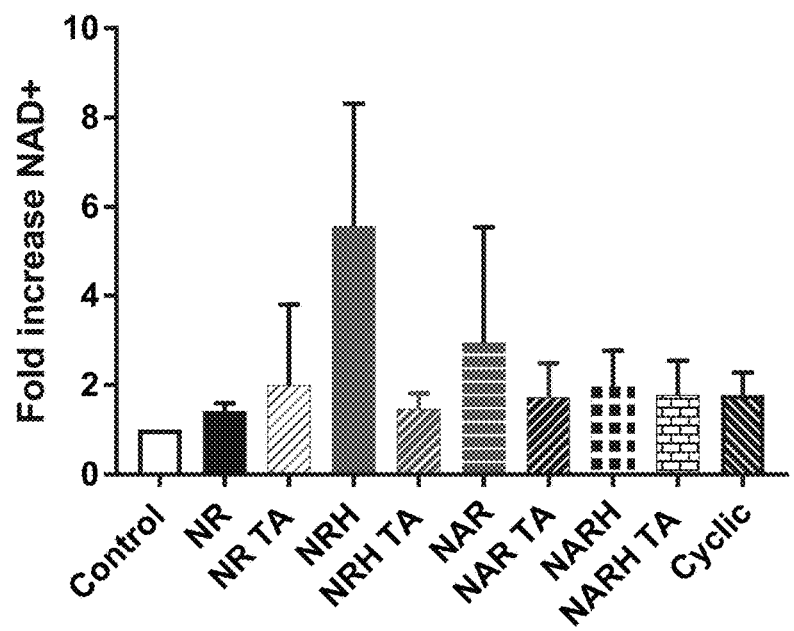
FIG. 9 depicts the Hela cell culture of FIG. 8 as a fold-increase in NAD over control.

Further, FIG. 9 presents the same data as a fold-increase in NAD over control. FIG. 8 presents a measurement of absolute NAD values (μM) in Hela cells (n=4) cultured in growth media supplemented with 100 μM of the corresponding NAD+ precursor (nicotinyl riboside test compound) for 24 hours, versus control (NAD content in cells measured in the absence of treatment compound). A control value was determined for each replicate data set.

Example B

Materials and Methods: HepG2 Cell Culture

HepG2 cells (passages 5-10) were grown in cell culture medium EMEM with 10% FBS serum and 1% pen-strip. Cells were seeded in Corning (REF 353046) 6-well tissue culture plates with flat bottom low evaporation lid. A density of 3×10$^5$ cells per well containing 1 mL of culture medium was incubated for 24 hrs at 37° C. overnight. The wells were aspirated, washed with PBS and 2 mL of fresh cell culture media was added. Each well had 2 μL of a freshly prepared 100 mM solution of the corresponding NAD+ precursor (nicotinyl riboside test compound) in water to give a final concentration of 100 μM per well and incubated for 24 h at 37° C. The media was aspirated and the wells washed with PBS, and for each condition, 1×10$^5$ cells were isolated and analyzed using an ENZYCHROM™ NAD+/NADH ASSAY KIT (E2ND-100) (Lot number BH01A04) following the manufacturer protocol (BioAssay Systems, Hayward, Calif.).

Results and Discussion

Figure 10:
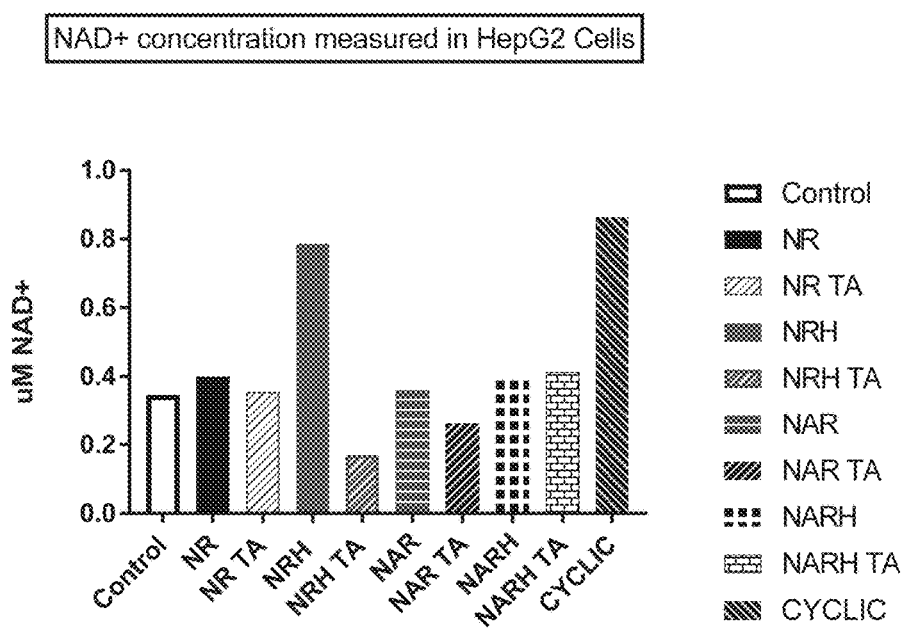
FIG. 10 depicts in another embodiment cultured HepG2 cells supplemented with an $NAD^+$ precursor (nicotinyl riboside test compound) for 24 hours, versus control.

As shown in FIG. 10, several of the nicotinyl derivatives demonstrated a profound and reproducible increase compared to control (NAD content in cells measured in the absence of treatment compound). FIG. 10 presents a measurement of absolute NAD values (μM) in HepG2 cells cultured in growth media supplemented with 100 μM of the corresponding NAD+ precursor (nicotinyl riboside test compound) for 24 hours, versus control (NAD content in cells measured in the absence of treatment compound). A control value was determined for each replicate data set.

The use of the terms "a," "an," "the," and similar referents in the context of describing the presently claimed invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof and, accordingly, reference should be made to the appended claims, rather than to the foregoing specification, as indicating the scope of the invention.

We claim:

1. A method for increasing intracellular NAD+ in a subject mammal, comprising delivering to the mammal in need of such treatment an effective amount of at least one compound of formula (I-Ha), or a salt, solvate, or prodrug thereof:

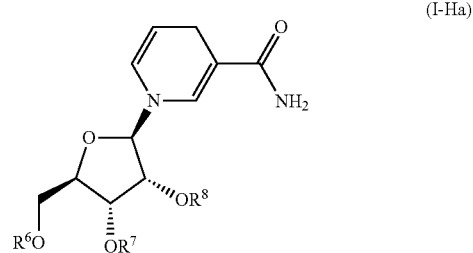

(I-Ha)

wherein R$^6$ is selected from the group consisting of hydrogen, —C(O)R', —C(O)OR', —C(O)NHR', substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, and substituted or unsubstituted heterocycle;

R' is selected from the group consisting of hydrogen, —(C$_1$-C$_8$)alkyl, —(C$_3$-C$_8$)cycloalkyl, aryl, heteroaryl, heterocycle, aryl(C$_1$-C$_4$)alkyl, and heterocycle(C$_1$-C$_4$) alkyl; and R$^7$ and R$^8$ are independently selected from the group consisting of hydrogen, —C(O)R', —C(O)OR', —C(O) NHR', substituted or unsubstituted (C$_1$-C$_8$)alkyl, substituted or unsubstituted (C$_3$-C$_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl;
provided that when $R^6$ is —C(O)R', and R' is —($C_1$-$C_8$)alkyl, then each of $R^7$ and $R^8$ is not hydrogen or —C(O)R' or —C(O)OR';
further provided that when $R^6$ is —C(O)OR', and R' is —($C_1$-$C_8$)alkyl, then each of $R^7$ and $R^8$ is not hydrogen or —C(O)R' or —C(O)OR'; or
a compound of formula (II-Hc), or a salt, solvate, or prodrug thereof:

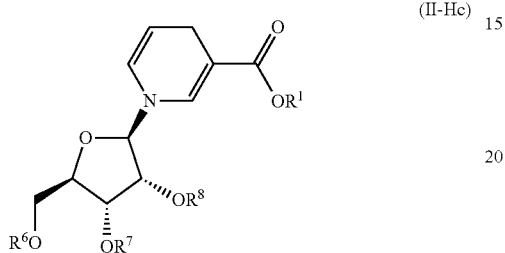

(II-Hc)

wherein $R^6$ is selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, and substituted or unsubstituted heterocycle;
R' is selected from the group consisting of hydrogen, —($C_1$-$C_8$)alkyl, —($C_3$-$C_4$)cycloalkyl, aryl, heteroaryl, heterocycle, aryl($C_1$-$C_4$)alkyl, and heterocycle($C_1$-$C_4$)alkyl; and
$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, substituted or unsubstituted heterocycle, substituted or unsubstituted aryl($c_1$-$C_4$)alkyl, and substituted or unsubstituted heterocycle($C_1$-$C_4$)alkyl and wherein $R^1$ is selected from hydrogen and ($C_1$-$C_4$) alkyl;
wherein NAD+ biosynthesis is increased.

2. The method according to claim 1, wherein the compound of formula (II-Hc) is NARH or NARH-TA.

3. A method for increasing intracellular NAD+ in a subject mammal, comprising
delivering to the mammal in need of such treatment an effective amount of at least one compound of formula (Ia), or a salt, solvate, or prodrug thereof:

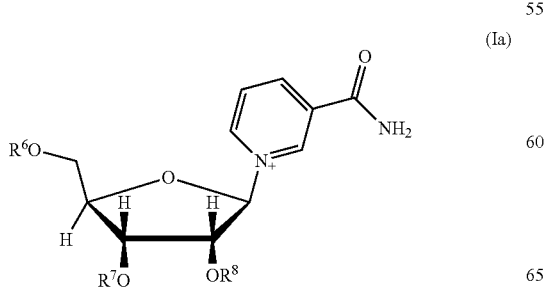

(Ia)

wherein $R^6$ is selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, and substituted or unsubstituted heterocycle;
R' is selected from the group consisting of hydrogen, —($C_1$-$C_8$)alkyl, —($C_3$-$C_8$)cycloalkyl, aryl, heteroaryl, heterocycle, aryl($C_1$-$C_4$)alkyl, and heterocycle($C_1$-$C_4$) alkyl; and
$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, substituted or unsubstituted heterocycle, substituted or unsubstituted aryl($C_1$-$C_4$)alkyl, and substituted or unsubstituted heterocycle($C_1$-$C_4$)alkyl;
provided that $R^6$, $R^7$, and $R^8$ are not all simultaneously hydrogen;
further provided that when $R^6$ is —C(O)R', and R' is —($C_1$-$C_8$)alkyl, then each of $R^7$ and $R^8$ is not hydrogen or —C(O)R' or —C(O)OR';
further provided that when $R^6$ is —C(O)OR', and R' is —($C_1$-$C_8$)alkyl, then each of $R^7$ and $R^8$ is not hydrogen or —C(O)R' or —C(O)R'; or
a compound of formula (IIa), or a salt, solvate, or prodrug thereof:

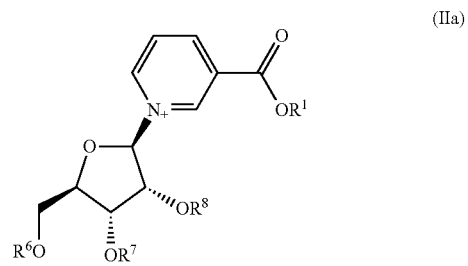

(IIa)

wherein $R^6$ is selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, and substituted or unsubstituted heterocycle;
R' is selected from the group consisting of hydrogen, —($C_1$-$C_8$)alkyl, —($C_3$-$C_4$)cycloalkyl, aryl, heteroaryl, heterocycle, aryl($C_1$-$C_4$)alkyl, and heterocycle($C_1$-$C_4$)alkyl; and
$R^7$ and $R^8$ are independently selected from the group consisting of hydrogen, —C(O)R', —C(O)OR', —C(O)NHR', substituted or unsubstituted ($C_1$-$C_8$)alkyl, substituted or unsubstituted ($C_3$-$C_8$)cycloalkyl, substituted or unsubstituted aryl, substituted or unsubstituted heteroaryl, substituted or unsubstituted heterocycle, substituted or unsubstituted aryl($c_1$-$C_4$)alkyl, and substituted or unsubstituted heterocycle($C_1$-$C_4$)alkyl and wherein $R^1$ is selected from hydrogen and ($C_1$-$C_4$) alkyl;
provided that $R^1$, $R^6$, $R^7$, and $R^8$ are not all simultaneously hydrogen;
wherein NAD+ biosynthesis is increased.

4. The method according to claim 3, wherein the compound of formula (IIa) is NARTA.

5. A method for increasing intracellular NADH in a subject mammal, comprising delivering to the mammal in need of such treatment an effective amount of at least one compound of formula (I-Ha), or a salt, solvate, or prodrug thereof:

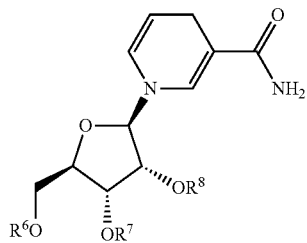

(I-Ha)

wherein $R^6$ is selected from the group consisting of hydrogen, —C(O)R', —C(O)OR', —C(O)NHR', substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle;

R' is selected from the group consisting of hydrogen, —$(C_1-C_8)$alkyl, —$(C_3-C_8)$cycloalkyl, aryl, heteroaryl, heterocycle, aryl$(C_1-C_4)$alkyl, and heterocycle$(C_1-C_4)$alkyl; and $R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_3-C_8)$cycloalkyl, substituted or unsubstituted aryl, substituted or unsubstituted heteroaryl, substituted or unsubstituted heterocycle, substituted or unsubstituted aryl$(C_1-C_4)$alkyl, and substituted or unsubstituted heterocycle$(C_1-C_4)$alkyl; or a compound of formula (II-Hc), or a salt, solvate, or prodrug thereof:

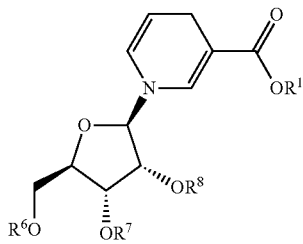

(II-Hc)

wherein $R^6$ is selected from the group consisting of hydrogen, —C(O)R', —C(O)OR', —C(O)NHR', substituted or unsubstituted $(C_1-C_8)$alkyl, substituted or unsubstituted $(C_3-C_8)$cycloalkyl, substituted or unsubstituted aryl, substituted or unsubstituted heteroaryl, and substituted or unsubstituted heterocycle;

R' is selected from the group consisting of hydrogen, —$(C_1-C_8)$alkyl, —$(C_3-C_4)$cycloalkyl, aryl, heteroaryl, heterocycle, aryl$(C_1-C_4)$alkyl, and heterocycle$(C_1-C_4)$alkyl; and $R^7$ and $R^8$ are independently selected from the group consisting of hydrogen, —C(O)R', —C(O)OR', —C(O)NHR', substituted or unsubstituted $(C_1-C_8)$alkyl, substituted or unsubstituted $(C_3-C_8)$cycloalkyl, substituted or unsubstituted aryl, substituted or unsubstituted heteroaryl, substituted or unsubstituted heterocycle, substituted or unsubstituted aryl$(c_1-C_4)$alkyl, and substituted or unsubstituted heterocycle$(C_1-C_4)$alkyl and wherein $R^1$ is selected from hydrogen and $(C_1-C_4)$alkyl;

wherein NADH biosynthesis is increased.

6. The method according to claim 5, wherein the compound of formula (I-Ha) is NRH or NRH-TA.

7. The method according to claim 5, wherein the compound of formula (II-Hc) is NARH or NARH-TA.

8. A method for increasing intracellular NAD+ in a subject mammal, comprising delivering to the mammal in need of such treatment an effective amount of NRTA, or a salt, solvate, or prodrug thereof, wherein NAD+ biosynthesis is increased.

* * * * *

UNITED STATES PATENT AND TRADEMARK OFFICE
CERTIFICATE OF CORRECTION

PATENT NO. : 10,183,036 B2
APPLICATION NO. : 15/492952
DATED : January 22, 2019
INVENTOR(S) : Ryan Dellinger et al.

It is certified that error appears in the above-identified patent and that said Letters Patent is hereby corrected as shown below:

In the Claims

In Column 33, Line 33, Column 34, Line 50, and Column 36, Line 20, replace "-($C_3$-$C_4$)cycloalkyl" with -- -($C_3$-$C_8$)cycloalkyl--.

In Column 33, Line 42, Column 34, Line 59, and Column 36, Line 29, replace "aryl($c_1$-$C_4$)alkyl" with --aryl($C_1$-$C_4$)alkyl--.

Signed and Sealed this
First Day of November, 2022

*Katherine Kelly Vidal*
Katherine Kelly Vidal
*Director of the United States Patent and Trademark Office*